(12) United States Patent
Hall et al.

(10) Patent No.: US 12,357,592 B2
(45) Date of Patent: Jul. 15, 2025

(54) COMPOSITIONS AND METHODS FOR MONITORING THE TREATMENT OF BREAST DISORDERS

(71) Applicants: Per Hall, Stockholm (SE); Mikael Eriksson, Täby (SE)

(72) Inventors: Per Hall, Stockholm (SE); Mikael Eriksson, Täby (SE)

( * ) Notice: Subject to any disclaimer, the term of this patent is extended or adjusted under 35 U.S.C. 154(b) by 1013 days.

(21) Appl. No.: 16/962,797

(22) PCT Filed: Jan. 24, 2019

(86) PCT No.: PCT/IB2019/050606
§ 371 (c)(1),
(2) Date: Jul. 16, 2020

(87) PCT Pub. No.: WO2019/145896
PCT Pub. Date: Aug. 1, 2019

(65) Prior Publication Data
US 2020/0360312 A1      Nov. 19, 2020

Related U.S. Application Data

(60) Provisional application No. 62/622,029, filed on Jan. 25, 2018.

(51) Int. Cl.
| | | |
|---|---|---|
| *A61K 31/138* | (2006.01) | |
| *A61B 5/00* | (2006.01) | |
| *A61B 5/055* | (2006.01) | |
| *A61B 6/03* | (2006.01) | |
| *A61B 6/50* | (2024.01) | |

(Continued)

(52) U.S. Cl.
CPC .......... *A61K 31/138* (2013.01); *A61B 5/004* (2013.01); *A61B 5/055* (2013.01); *A61B 6/032* (2013.01); *A61B 6/502* (2013.01); *G06T 7/0014* (2013.01); *G06T 7/136* (2017.01); *G06T 7/33* (2017.01); *G06T 7/97* (2017.01); *G16H 20/10* (2018.01); *G16H 30/40* (2018.01); *G16H 50/20* (2018.01);

(Continued)

(58) Field of Classification Search
CPC .................. A61B 5/0091; A61B 10/0041
See application file for complete search history.

(56) References Cited

U.S. PATENT DOCUMENTS

| | | |
|---|---|---|
| 9,311,717 B2 | 4/2016 | Serlie et al. |
| 9,615,805 B2 | 4/2017 | Behiels |

(Continued)

FOREIGN PATENT DOCUMENTS

| | | |
|---|---|---|
| JP | 0737074 | 2/1995 |
| JP | 2009090094 | 4/2009 |

(Continued)

OTHER PUBLICATIONS

AU2019212585, "First Examination Report", May 4, 2021, 4 pages.

(Continued)

*Primary Examiner* — Wen W Huang
(74) *Attorney, Agent, or Firm* — Kilpatrick Townsend & Stockton LLP

(57) ABSTRACT

Disclosed herein are systems, media, and methods for processing and aligning breast images and uses thereof. The processes disclosed herein may be used to diagnose, predict, and monitor the status or outcome of breast density masking, and breast cancer in a subject, and methods of treating the same.

26 Claims, 9 Drawing Sheets

General Alignment Process Overview

(51) Int. Cl.
*G06T 7/00* (2017.01)
*G06T 7/136* (2017.01)
*G06T 7/33* (2017.01)
*G16H 20/10* (2018.01)
*G16H 30/40* (2018.01)
*G16H 50/20* (2018.01)
*G16H 50/50* (2018.01)

(52) U.S. Cl.
CPC ... *G16H 50/50* (2018.01); *G06T 2207/20081* (2013.01); *G06T 2207/30068* (2013.01)

(56) References Cited

U.S. PATENT DOCUMENTS

| | | |
|---|---|---|
| 2006/0245629 A1 | 11/2006 | Huo et al. |
| 2009/0060300 A1 | 3/2009 | Neemuchwala et al. |
| 2009/0220139 A1 | 9/2009 | Schneider et al. |
| 2010/0298694 A1 | 11/2010 | Marrouche et al. |
| 2011/0026791 A1* | 2/2011 | Collins .............. G06T 7/136 382/131 |
| 2011/0188726 A1* | 8/2011 | Nathaniel ............ A61B 6/4441 378/42 |
| 2011/0243409 A1* | 10/2011 | Naimi .............. A61B 5/0091 382/128 |
| 2013/0038629 A1 | 2/2013 | Lautenschläger et al. |
| 2013/0230230 A1* | 9/2013 | Ajemba .............. G06T 7/155 382/133 |
| 2015/0023576 A1 | 1/2015 | Behiels |
| 2015/0036906 A1 | 2/2015 | Kim et al. |
| 2016/0019690 A1 | 1/2016 | Bediz et al. |
| 2016/0284071 A1* | 9/2016 | Udupa .................. G06T 5/50 |
| 2018/0285531 A1* | 10/2018 | Korn ................. G16H 50/30 |
| 2019/0209497 A1* | 7/2019 | Ma .................... A61K 31/4535 |

FOREIGN PATENT DOCUMENTS

| | | |
|---|---|---|
| JP | 2012135444 | 7/2012 |
| JP | 2017527775 | 9/2017 |
| KR | 20110039896 A | 4/2011 |
| WO | 2010079519 | 7/2010 |
| WO | WO-2012112627 A2 | 8/2012 |

OTHER PUBLICATIONS

Der, "3D Digital Analysis of Mammographic Composition", Available Online at, URL: https://elib.uni-stuttgart.de/bitstream/11682/2658/1/Lampasona_Diss.pdf, 2009, 126 pages.

Eriksson et al., "A Comprehensive Tool for Measuring Mammographic Density Changes Over Time", Breast Cancer Research and Treatment, vol. 169, No. 2, Feb. 1, 2018, pp. 371-379.

Lin, "Assessing Breast Density Changes Over Time", European Society of Radiology, Available Online at: URL:https:jposterng.netkey.atjesrjviewing/index.php?module=viewing_posteraction&task=downloadpdf&pi=118070, Jan. 1, 2013, 14 pages.

Lazzeroni et al., "Oral Low Dose And Topical Tamoxifen For Breast Cancer Prevention: Modern Approaches For An Old Drug", Breast Cancer Research, vol. 14, No. 214, Available Online at, URL:https://breast-cancer-research.biomedcentral.com/track/pdf/10.1186/bcr3233, Oct. 29, 2012, 12 pages.

Li et al., "Mammographic Density Reduction Is a Prognostic Marker of Response to Adjuvant Tamoxifen Therapy in Postmenopausal Patients With Breast Cancer", Journal Of Clinical Oncology, Original Report, vol. 31, No. 18, Jun. 20, 2013, pp. 2249-2256.

PCT/IB2019/050606, International Preliminary Report on Patentability, Mailed On Aug. 6, 2020, 12 pages.

PCT/IB2019/050606, International Search Report and Written Opinion, Mailed On Jun. 3, 2019, 16 pages.

* cited by examiner

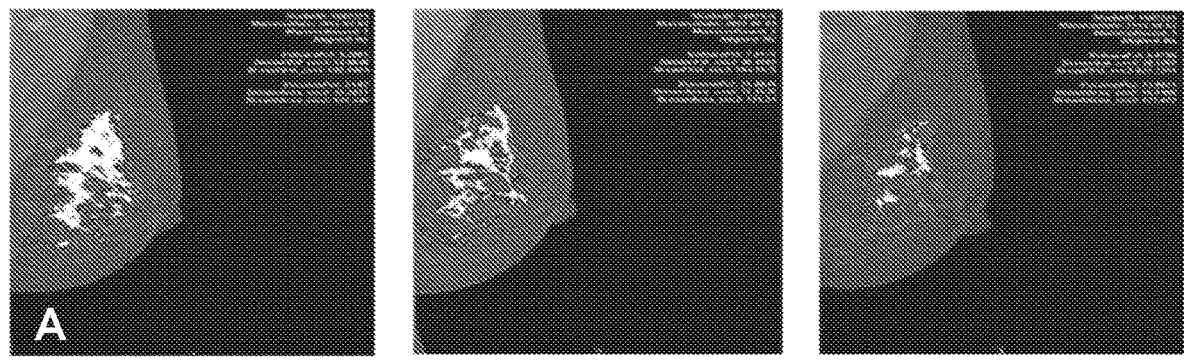
FIG. 3A
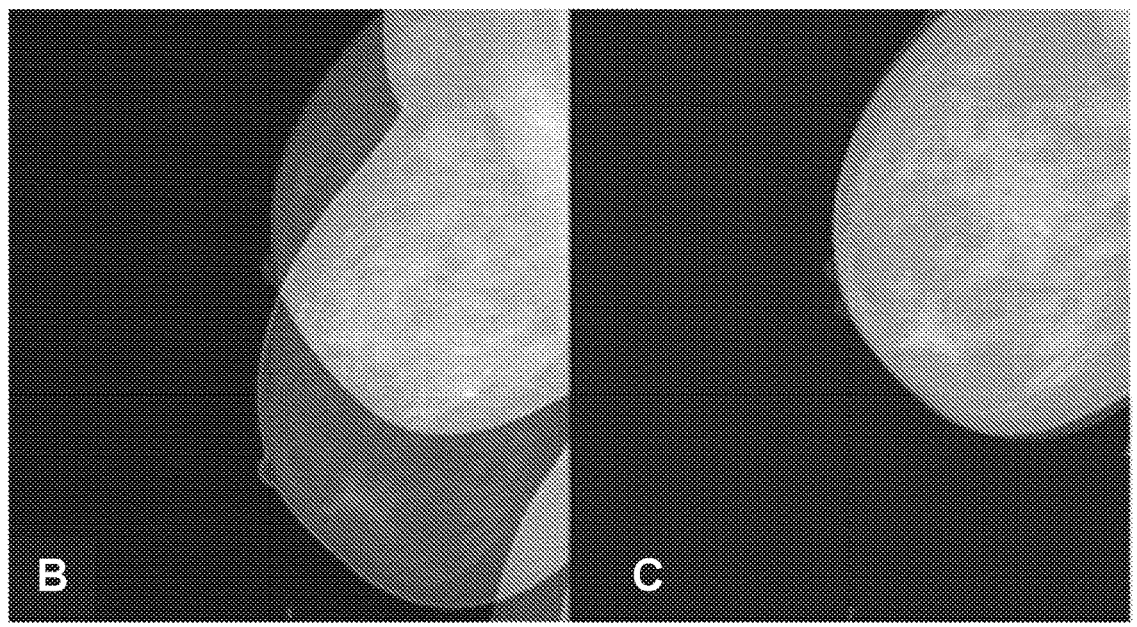
FIG. 3B                    FIG. 3C

Premenopausal

Postmenopausal

COMPOSITIONS AND METHODS FOR MONITORING THE TREATMENT OF BREAST DISORDERS

RELATED APPLICATIONS

The present application is a U.S. 371 Application of International Application No. PCT/IB2019/050606, filed Jan. 24, 2019, which application claims the benefit of the filing and priority dates of U.S. Provisional Application No. 62/622,029, filed Jan. 25, 2018, the contents of which are hereby incorporated by reference in their entirety for all purposes.

BACKGROUND

Anti-hormonal compounds such as selective estrogen receptor modulators (e.g. tamoxifen) and aromatase inhibitors are used for prevention and as adjuvant therapy for breast cancer. Adjuvant therapy is given in addition to the primary therapy to reduce the risk of a recurrence. Adjuvant therapy is given when all detectable disease has been removed, but where there remains a risk of relapse due to the presence of undetected disease. If no disease is left behind following surgery and other treatment, then further treatment is not by definition adjuvant. Tamoxifen as prevention for breast cancer has been tested in a number of trials and proven to reduce the risk of breast cancer by as much as 50% when given to healthy women. When tamoxifen is administered for prevention or adjuvant therapy, it has previously not been possible to monitor the effect of therapy for the simple reason that there is no detectable disease to follow.

Mammographic density is the white (radiographically opaque) part of the mammogram consisting of fibroglandular tissue. It is well known in the art that mammographic density is closely linked to the risk of breast cancer. Women with high density have a nearly 6-fold higher risk of breast cancer compared to those with very little density seen in a mammogram. In addition, a handful of studies have over the last years shown that tamoxifen influences mammographic density in a large proportion of the treated women, whether healthy women using tamoxifen for prevention or breast cancer patients under adjuvant therapy. The data suggest that only women with reduced mammographic density respond to tamoxifen therapy. Mammographic density could thus not only be used as a risk factor but as a proxy for therapy response.

Breast density is identified by visual techniques such as mammography and reflects increased fibroglandular tissue within the breast, i.e., growth of stromal and epithelial cells in the breast. Breast density is clinically classified in 4 classes Class A (the breasts are almost entirely fatty), B (there are scattered areas of fibroglandular density), C (the breasts are heterogeneously dense, which may obscure small masses), and D (the breasts are extremely dense, which lowers the sensitivity of mammography, i.e. masking) (ACR BI-RADS Atlas 5$^{th}$ Edition, breast composition, 2013) based on the degree of severity of the density.

At least 30 states in USA require physicians to inform subjects if they have dense breast(s). There are currently no established routines for changing or decreasing breasts density, although subjects are reminded to make healthy lifestyle choices, undergo regular mammograms to monitor changes in breast density and consider to undergo additional examinations such as ultrasound.

Presence in breast density can mask the detection of breast disorders such as breast cancer in a subject. In addition, High mammographic density in itself is a strong risk factor for breast cancer [Boyd et al. J. Natl. Cancer Inst. 1995, May 3:87(9):670:5]. The dense area in the breast consisting of epithelium and stroma is radiographically dense. Epithelium and stroma appears bright on a mammogram while the fatty tissue is radiolucent and appears dark. In addition to being a marker of breast cancer risk, density change has been shown to be a good proxy for response to therapy, such as endocrine therapy, both in the preventive (Cuzick et al. J. Natl. Cancer Inst. 2011 May 4:103(9): 744-52) and adjuvant setting (Li et al. J. Clin. Oncol. 2013, June 20:31(18):2249-56, Nyante et al. J. Natl. Cancer Inst. 2015 Feb. 6; 107(3)). Patients or healthy individuals that respond to endocrine therapy have a significant lowering of density compared to non-responders.

However, mammographic density is, for different reason, currently measured sub-optimally. Firstly, mammograms from the same woman at different time points are not always comparable since dissimilar proportions of the breast could be captured in the images. A difference in density with non-biological implications or artifacts are captured. Secondly, measurements of mammographic density at any point in time is not comparable since the measurement is strongly affected by how much the breast was compressed in the mammography machine while taking the mammogram. The compression routines are decided individually by the hospital radiographer, and the thickness of the compressed breast is reported inconsistently between vendors of the mammography machines. A density measurement method which does not control for the breast compression and does not normalize the machine reported thickness of the compressed breast therefore captures a non-biological component into the measure.

Radiologists and other medical personnel examine mammographic images to identify various abnormalities in a breast. Cumulus is the gold standard to measure mammographic density on analogue mammograms (Byng et al. Radiographics. 1998; 18:1587-98). The drawbacks of Cumulus are that it does not account for the dissimilar breast proportions in the images, it does not account for compression and thickness of the compressed breast, it is labor intense, and is heavily dependent on the experience of the reader (Burton et al. Breast Cancer Res. 2016; 18:130).

Several commercial tools measure density automated on digital raw mammograms, but still with the same concern of capturing non-biological differences [Chen et al. Transl. Oncol. 2015 Dec. 8(4435-445]. Raw images are available only during a short time frame in the hospital work-flow before they are converted to processed images. Vendors of mammography machines such as GE, Hologic, Philips, Sectra and Siemens use different conversion methods which makes processed images difficult to compare.

When analyzing mammographic images in a digital mammography system, images are displayed in a digital workstation and it is possible to compare mammograms from different examinations. The images used for comparison, while of the same object, may be acquired at different times, acquired with different imaging systems and/or acquired using different display settings.

Different types of image alignment protocols have been employed for displaying mammographic images of the breast for comparison. For example, one alignment protocol for images in the cranio-caudal view may involve placing the left and right cranio-caudal breast views next to each other so that the chest walls will meet on the central vertical axis of the viewport. Similar arrangements, known to those skilled in the art, also exist for mediolateral oblique views.

Other image alignment strategies include alignment based on anatomical features of the breast, for example, the nipple and/or the chest wall. In cranio-caudal images, for example, the nipple located in each pair of images may be positioned so that they are horizontally aligned, that is, at the same height. For mediolateral oblique images, either the nipple or pectoralis may be chosen as features used for alignment.

Several patents and applications describe methods of processing mammographic images. US20090220139A1 describes a means for detecting a contour line that surrounds an object area of the mammogram, which is defined by an object.

U.S. Pat. No. 9,311,717B2 describes a system for processing and displaying a breast image with overlaid glandular contour.

US20160019690A1 describes a method and system for aligning plurality of physically scaled mammography images.

U.S. Pat. No. 9,615,805 and US20150023576A1 describe a method of aligning at least two breast images on the basis of shape analysis procedures performed on the breast images.

There is currently no automated tool that measures density of the processed images regardless of vendor and accounts for alignment and breast compression. This is unfortunate since most digital images are stored as processed images and precise measures are needed to monitor treatment response and density change over time.

SUMMARY

Described herein are methods and systems that facilitate efficient diagnostic reviews of mammography images, regardless of the images' provenance. The methods and systems described herein allow radiologists and other medical personnel to quickly compare and detect differences between mammograms, for instance mammographic density, and report their findings within clinically acceptable time frames. The methods and systems described herein provide an improvement for measuring the density change over time since density change has proven to be a reliable and strong proxy for therapy response. The methods and systems described herein provide improved methods for processing breast images for diagnosing, predicting, and monitoring the status or outcome of a breast disorder such as breast cancer, and increase the ability to detect abreast disorder that is otherwise difficult to detect due to mammographic breast density (MBD) masking.

As such, it is desirable to have mammography systems that facilitate efficient diagnostic reviews of mammography images, regardless of its provenance, so as to allow them to quickly compare and detect differences, for instance mammographic density, between mammograms and report their findings within clinically acceptable time frames.

The methods and systems described herein address an unmet medical need, namely by providing an automated tool that measures density of the processed images regardless of vendor and accounts for alignment and breast compression. Thus, in one aspect, the present disclosure provides a computer-implemented method, comprising: (a) receiving, in a computer processing system, data input comprising a plurality of breast images and image metadata of a subject; and (b) applying an alignment algorithm to the plurality of breast images, the alignment algorithm further comprising: (i) performing a thresholding method on the plurality of breast images marking breast area in the plurality of breast images; (ii) superimposing the breast area in each of the plurality of breast images in layers; (iii) moving binary masks in breast area markings towards each other to an optimal position for alignment of the breast areas where the pixel intensities of breast images show minimal difference relative to one another; and (iv) generating by computer an aligned image comprising an area of mutual image information.

In another aspect, provided herein is a non-transitory computer-readable media storing thereon executable instructions, that when executed by a computer, causes the computer to execute a method for aligning a plurality of breast images of a subject, the method comprising: (a) obtaining a data input comprising a plurality of breast images and image metadata; (b) applying an alignment algorithm to the plurality of breast images, the alignment algorithm comprising: (i) performing a thresholding method on the plurality of breast images marking breast area in the plurality of breast images; (ii) superimposing the breast area in each of the plurality of breast images in layers; (iii) moving binary masks in breast area markings towards each other to an optimal position of alignment where the pixel intensities of breast images show minimal difference relative to one another; and (iv) generating an aligned image comprising an area of mutual image information; and (c) determining density measures from the area of mutual image information in the aligned image based on a statistical machine learning model.

In any of the embodiments described herein, the data input can comprise a plurality (e.g., two or more) of breast images and image metadata obtained over a time period, for example, over a time period in which the same women is monitored for a breast disorder. Thus, in some embodiments, the method further comprises (d) presenting the density measures over a time period, e.g., a monitored time period. In some embodiments, the method further comprises (e) displaying the density measures over the time period, e.g., a monitored time period. The density measures can be presented or displayed to a clinician, such as a radiologist or attending physician, or to the subject, for example, a patient.

In some embodiments, the methods further comprise extracting texture features from mutual image information of the breast area in (i) an aligned image or (ii) each of the plurality of breast images. In some embodiments, the texture features are further stratified and compiled to generate feature variables. In some embodiments, the image metadata comprises reported thickness of the compressed breast, reported x-ray tube voltage of the machine, mammography machine type, and machine specific breast thickness compression constants, or a combination thereof. In some embodiments, the present disclosure provides computer-implemented methods comprising obtaining a plurality of breast images and image metadata and applying a breast compression score algorithm to a plurality of breast images based on image metadata to generate a breast compression score.

In some embodiments, the methods further comprise generating a biomedical output comprising density measures from the area of mutual image information in the aligned image, determined based on a statistical machine learning model. In some embodiments, the breast image is a 2D image, a 3D image, an MRI image, a CT-Scan image, or a mammographic image. In some embodiments, the mammographic image is a digital image, an analog image, a raw image, a processed image, a normalized image, or a digitally scaled image.

In some embodiments, the methods further comprise: (a) generating a first aligned image and a second aligned image of the subject's breast; and (b) comparing average density measures from the area of mutual image information of the second aligned image relative to average density measures from the area of mutual image information of the first aligned image. In some embodiments, the first aligned image is of the subject's right breast and the second aligned image of the subject's left breast. In other embodiments, the first aligned image of the subject's breast is from a reference time and the second aligned image is from the target time.

In some embodiments, the methods described herein further comprise designating a treatment regimen for the subject based at least in part on the aligned image. In some embodiments, the methods described herein further comprise providing treatment in accordance with a designated treatment regimen based at least in part on the aligned image. It will be understood that designating a treatment regimen and providing a treatment in accordance with the designated treatment regimen can include providing instructions to a clinician or physician, or the act of administering the treatment to the subject or patient. Exemplary treatment regimens are described herein.

In some embodiments, the methods described herein further comprise providing for presentation information to facilitate treatment of the subject based at least in part on the aligned image. In some embodiments, the methods described herein further comprise providing for graphical presentation of diagnostic information to facilitate treatment of the subject based at least in part on the aligned image such that the information improves detection of changes over time relative to comparable information based on non-aligned, or differently aligned, images.

In one aspect, a non-transitory computer-readable storage media encoded with a computer program including instructions executable by a digital processing device is provided, the non-transitory computer-readable storage media comprising: (a) a software module configured to obtain input data comprising a plurality of breast images and image metadata of a subject; (b) a software module configured to apply an alignment algorithm comprising (i) performing a thresholding method on the plurality of breast images to mark breast area in the breast images; (ii) superimposing the breast area in each of the plurality of breast images in layers; (iii) moving binary masks towards each other to an optimal position where the pixel intensities of the breast images show minimal difference relative to one another; (iv) generating an aligned image comprising an area of mutual image information; and (c) a software module for determining density measures from the area of mutual image information.

As above, in some embodiments, the software module presents or displays the density measures over a time period, for example, over a time period in which the same women is monitored for a breast disorder. Thus, in some embodiments, the software module is further configured to (d) present the density measures over a time period, e.g., a monitored time period. In some embodiments, the software module is further configured to (e) display the density measures over a time period, e.g., a monitored time period. As above, the density measures can be presented or displayed a clinician, such as a radiologist or attending physician, or to the subject, for example, a patient.

In some embodiments, the non-transitory computer-readable storage media further comprises one or more software modules configured to generate a breast compression score by applying a breast compression score algorithm to the mutual image information. In other embodiments, the non-transitory computer-readable storage media further comprises a software module configured to designate a treatment regimen for the subject.

In another aspect, a computer-implemented system is provided, comprising: (a) a digital processing device comprising an operating system configured to perform executable instructions, and a memory device; (b) a computer program including instructions executable by a digital processing device comprising; (i) a software module configured to receive a plurality of mammographic images of a subject; (ii) a software module configured to apply alignment algorithm to the plurality of images, the alignment algorithm comprising: (1) performing a thresholding method on the plurality of breast images to mark breast area in the breast images; (2) superimposing the breast area in each of the plurality of breast images in layers; (3) moving binary masks towards each other to an optimal position where the pixel intensities of the breast images show minimal difference relative to one another; and (4) generating an aligned image comprising an area of mutual image information; and (iii) a software module configured to analyze changes in breast density of a subject over time.

In some embodiments, the system further comprises one or more software modules configured to generate a breast compression score. In other embodiments, the system further comprises one or more software modules configured to generate a biomedical output comparing the breast density measures of the area of mutual image information of aligned images over time. In still other embodiments, the system further comprises one or more software modules configured to diagnose, predict, or monitor the status or outcome of breast density masking or breast cancer or both in a subject, designate a subject as a tamoxifen-responder or a tamoxifen-non-responder, and designate a treatment regimen for the subject.

In another aspect, described herein is a computer-implemented method for diagnosing, predicting or monitoring the status or outcome of a breast disorder in a subject, comprising determining the subject's breast density status according to a method described herein.

In another aspect, described herein is a computer-implemented method of designating a subject as a responder or non-responder to therapy comprising determining density measures of the subject over time to according to a method described herein. In some embodiments, the therapy is neo-adjuvant or adjuvant therapy comprising tamoxifen.

In another aspect, described herein is a method of treatment of a subject having or at risk of having a breast disorder, the method comprising: (a) testing the subject according to any of the methods described herein; and (b) delivering to the subject an effective amount of low-dose tamoxifen. In some embodiments, the low dose tamoxifen is 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg of tamoxifen per unit dose. In some embodiments, the low-dose tamoxifen is administered orally, topically, intraductally, or parenterally. In an aspect, the present invention provides that the low-dose tamoxifen reduces breast disorder.

In some embodiments, the breast disorder is breast density masking or breast cancer.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIGS. 3A, 3B, and 3C show mammograms of breast tissue. FIG. 3A shows an example where the size of the breast image is more or less similar in three different mammograms from the same subject. FIGS. 3B and 3C show two mammograms of the same breast taken 2 minutes apart by the same radiographer. In Frame A the mammograms were superimposed to show the difference in breast placement in the mammography machine. In Frame B, the two images were digitally aligned to the image showing the smallest breast size (upper breast outlined in Frame A) prior to density measurement, as described in the Examples.

In a sub analysis, BMI was substituted with breast area as adjustment factor. This showed the same mean percent mammographic density of 4.3 in raw and processed mammograms with non-significant differences between the machines (data not shown).

Figure 8A:
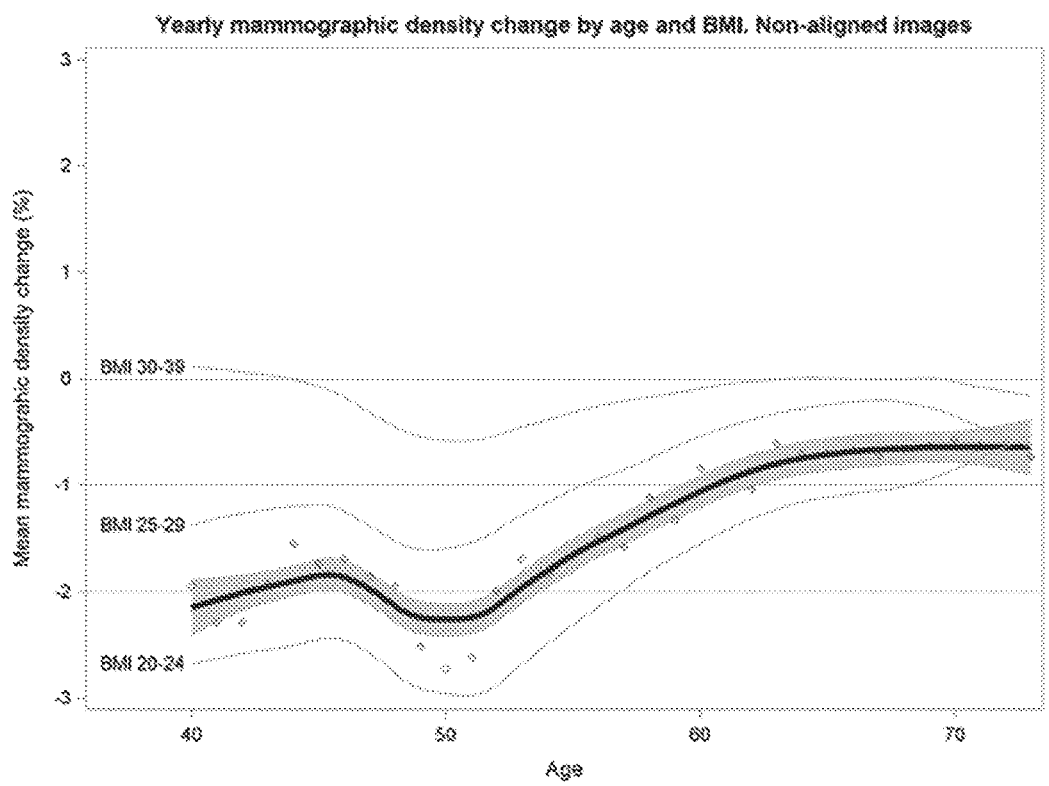
Figure 8B:
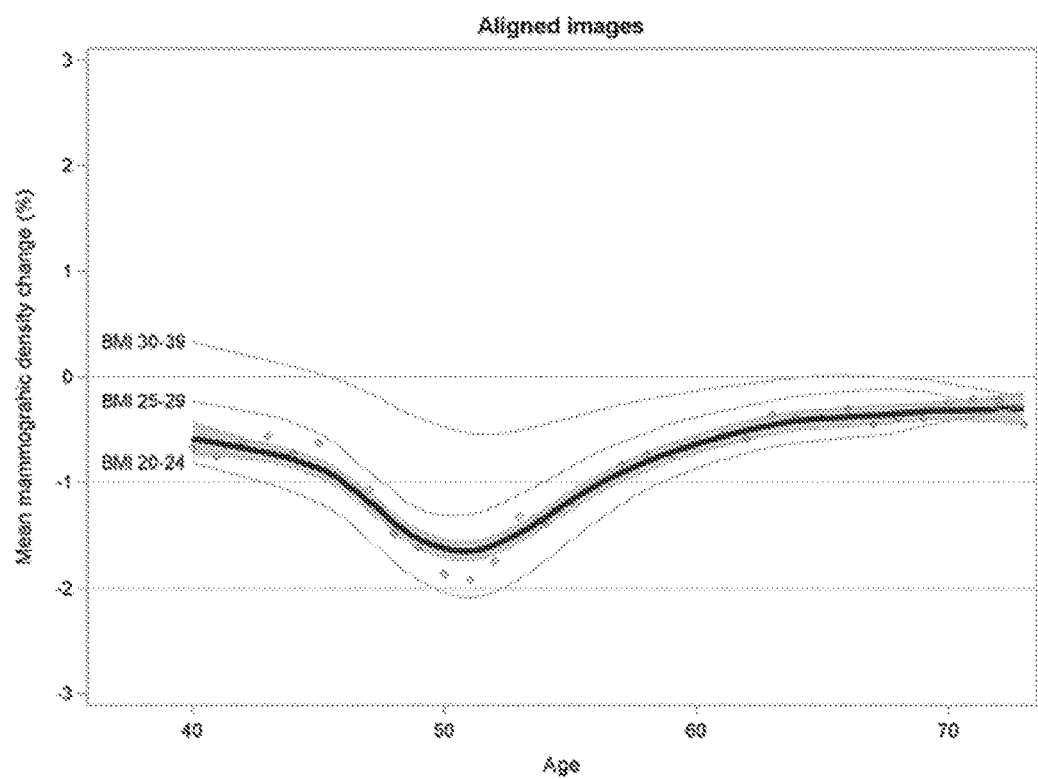

FIGS. 8A and 8B show non-aligned and aligned images using the methods described herein. Comparison of yearly percent mammographic density change in 55,073 women with aligned and non-aligned mammograms taken at two time-points one to two years apart. The blue fitted curve (non-linear regression) shows the yearly average percent density change with 95% CI. The circled dots show the density averages by age at baseline. The green curves show the density change stratified by BMI at baseline for women with BMI between 20 and 40. The aligned and non-aligned density changes showed more pronounced development in women aged 45 to 55. The yearly mean percent density decreases in the 40 year-old women, N=2,499, were 0.7 (95% CI 0.4-0.9) with the aligned density measure and 1.9 (95% CI 1.7-2.2) with the non-aligned density measure. The corresponding numbers for 50 year-old women, N=1,878, were 1.9 (CI 1.7-2.1) and 2.7 (CI 2.5-3.0).

Figure 9:
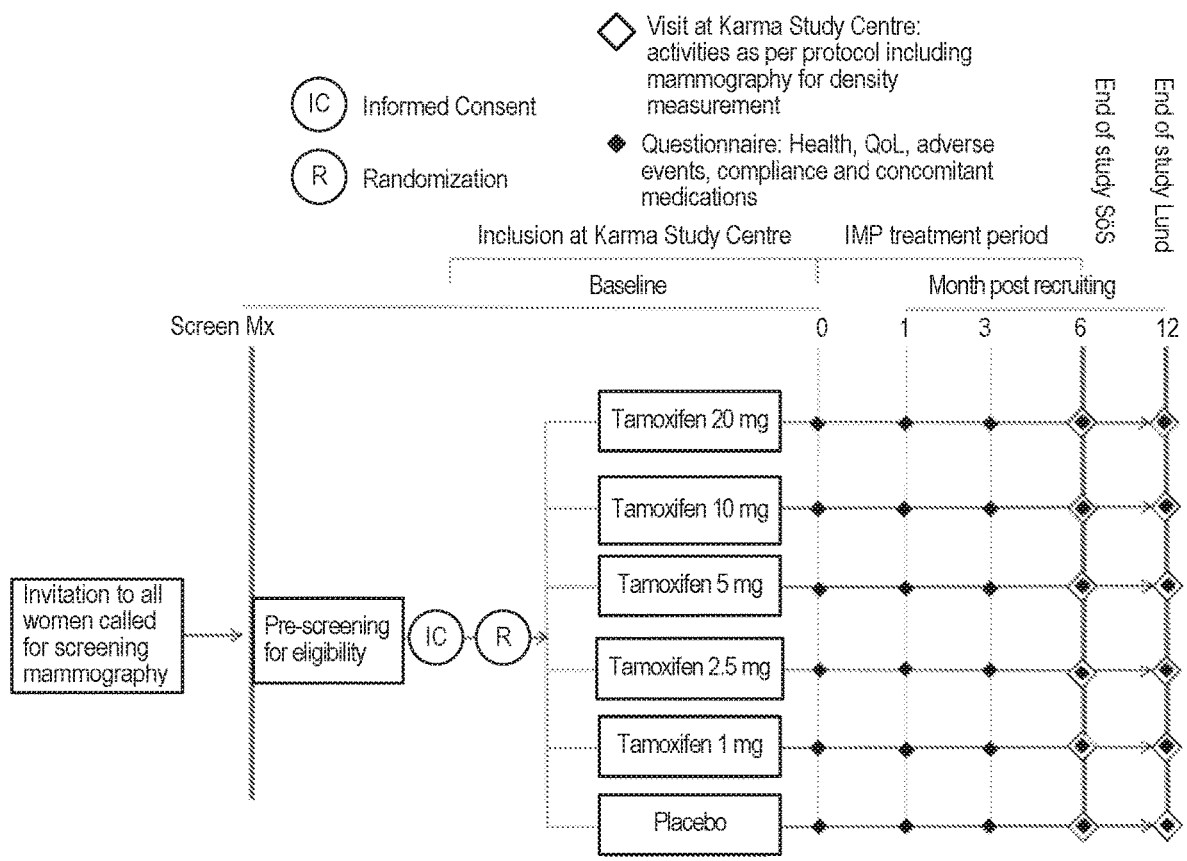

FIG. 9. Clinical Trial Design of Randomized, Double Blinded, Six-Armed Placebo Controlled Study of Low Dose Tamoxifen.

DEFINITIONS

As used herein, the terms "a," "an," and "the" include plural reference unless the context dictates otherwise.

As used herein, "preventive therapy" refers to a therapy that is administered to healthy individuals at increased risk of breast cancer in order to decrease the risk of being diagnosed with breast cancer.

As used herein, "adjuvant therapy" refers to a therapy that follows a primary therapy of breast cancer and that is administered to patients to decrease the risk of relapsing. Adjuvant systemic therapy in case of breast cancer usually begins soon after primary therapy to delay recurrence, prolong survival or cure a subject.

As used herein, "neo-adjuvant therapy" refers to a therapy that precedes surgery for breast cancer and is administered to patients in order to decrease the tumor burden.

As used herein, "breast density masking" refers to a tumor being hidden on a mammogram and not being detected due to the similar appearances of both mammographically dense regions and the tumor, thus, decreasing the sensitivity of mammography.

As used herein, the term "tamoxifen" refers to (Z)-2-[4-(1,2-diphenyl-1-butenyl)phenoxy]-N,N-dimethyl-ethanamine. Tamoxifen can also refer to E-isomer or a combination of E-isomer and Z-isomer.

As used herein and in the claims, the terms "comprising," "containing," and "including" are inclusive, open-ended and do not exclude additional unrecited elements, compositional components or method steps. Accordingly, the terms "comprising" and "including" encompass the more restrictive terms "consisting of" and "consisting essentially of"

As used herein, the term "dosage form" means the form in which the compounds or compositions of the present disclosure are delivered to a patient. The dosage form refers to the compounds or compositions of the present disclosure delivered to a subject in any form suitable for its route of administration or delivery, for example, without limitation, oral, parenteral, topical, transdermal, transpapillary and intraductal delivery.

As used herein, the terms "subject," "patient," and "individual," may be used interchangeably herein and refer to a mammal such as a human. Mammals also include pet animals such as dogs, cats, laboratory animals, such as rats, mice, and farm animals such as cows and horses. Unless otherwise specified, a mammal may be of any gender or sex.

As used herein, the term "unit dosage form" refers to physically discrete units suitable for unitary dosages for subjects, each unit containing a predetermined quantity of active material calculated to produce the desired therapeutic effect, in association with a suitable pharmaceutical excipient.

As used herein, a "unit dose" is a dose of any therapeutic or active agent administered in one dose/at one time/single route/single point of contact, i.e., one administration event. As used herein, "split dose" refers to (1) dosing regimens in which one or more active agents are administered to a patient at least twice daily; (2) once daily administration of a pharmaceutical composition containing one or more active agent in which a portion of the active agent is formulated for immediate release and a portion of the active agent is formulated for delayed or pulsatile release; and (3) once daily administration of a pharmaceutical composition containing an active agent formulated for controlled or sustained release.

As used herein, "breast disorder" refers to any breast disease, condition or disorder that is accompanied by breast density. For avoidance of doubt, for the purpose of this invention breast disorder includes breast density masking and breast cancer.

As used herein, "breast cancer" means any malignant tumor of breast cells. Breast cancer may be at any stage of breast cancer, including stages of a pre-cancer, an early stage cancer, a non-metastatic cancer, a pre-metastatic cancer, a locally advanced cancer, and a metastatic cancer. Breast cancer can be invasive breast cancer or in situ breast cancer. There are several types of breast cancer. Exemplary breast cancers include, but are not limited to, ductal carcinoma in situ (DCIS), lobular carcinoma in situ (LCIS), invasive (or infiltrating) lobular carcinoma (ILC), invasive (or infiltrating) ductal carcinoma (IDC), microinvasive breast carcinoma (MIC), inflammatory breast cancer, ER-positive (ER+) breast cancer, ER-negative (ER−) breast cancer, HER2+ breast cancer, triple negative breast cancer (TNBC), adenoid cystic (adenocystic) carcinoma, low-grade adenosquamatous carcinoma, medullary carcinoma, mucinous (or colloid) carcinoma, papillary carcinoma, tubular carcinoma, metaplastic carcinoma, or micropapillary carcinoma. A single breast cancer tumor can be a combination of these types or be a mixture of invasive and in situ cancer.

DCIS is the most common non-invasive breast cancer. It involves the cell lining the breast ducts. In DCIS, the cells have not spread beyond the walls of the duct into the surrounding breast tissue. About 1 in 5 new breast cancer cases will be DCIS. LCIS is a pre-cancerous neoplasia. It may be indicative of a predisposition for invasive cancer. LCIS only accounts for about 15% of the in situ (ductal or lobular) breast cancers.

IDC is the most invasive breast cancer. As the name applies, it is a carcinoma that begins in the breast ducts and then invades the surrounding fatty tissue. About 8 to 10 invasive breast cancers are infiltrating ductal carcinomas. IDC is often treated by surgery to excise the cancerous tissue, and radiation therapy. In addition, chemotherapy combined with endocrine therapy (e.g tamoxifen) and/or immunotherapy (e.g., tratuzumab) is often used to treat IDC.

ILC is a cancer that develops in the lobules of the breast and has invaded the surrounding tissue. About 1 in 10 invasive breast cancers is an ILC. ILC is treated by surgery to excise the cancerous tissue, and radiation therapy. In addition, chemotherapy combined with endocrine therapy (e.g tamoxifen) and/or immunotherapy (e.g., tratuzumab) is often used to treat ILC.

Inflammatory breast cancer accounts for about 1% to 3% of all breast cancers. In inflammatory breast cancer, cancer cells block lymph vessels in the skin resulting in the breast turning red and feeling warm. The affected breast may become larger or firmer, tender, or itchy. Inflammatory breast cancer is treated with chemotherapy, immunotherapy, radiation therapy and in some cases, surgery.

ER+ breast cancer is characterized by the presence of estrogen receptors on the surface of the cancerous cells. Growth of ER+ cancer cells is associated with the availability of estrogen (hormone-dependent or hormone sensitive breast cancer). Approximately, 80% of all breast cancers are ER+ breast cancers. Treatment options for ER+ breast cancer include endocrine agents such as tamoxifen that block the ER or aromatase inhibitors that reduces production of estrogen.

DETAILED DESCRIPTION

The present disclosure provides systems, media, and methods for diagnosing, predicting and monitoring the status and outcome of a breast disorder in a subject. In another aspect, the present disclosure also provides methods for designating a subject as a responder or a non-responder to therapy and treatment regimens.

In an advantageous aspect, the present disclosure provides systems, media, and methods for alignment of a plurality of breast images from a subject in need thereof and performing density measurements on the aligned images. In some embodiments, the systems, media, and methods further comprise assigning a breast compression score to the images using a breast compression score algorithm. The breast compression score in useful in determining the density measure using a statistical machine learning model as described below. In another aspect, the present disclosure provides systems, media, and methods for measuring changes in density measurements in the breast of a subject over time. In some embodiments, the methods are fully automated.

The systems, media, and methods described herein provide an unexpected advantage over prior methods. The instant methods allow for mammograms from the same women to be aligned such that the same or substantially the same amount of tissue is seen in the aligned images. FIG. 3A illustrates the case where size and orientation of three different breast images is substantially the same or similar. However, it is often the case that mammograms of the same women taken at different times and/or using different machines do not show the same part of the breast, or the size and/or orientation of the breast in each image is different. This is illustrated in FIG. 3B. This makes it difficult to determine if differences in density are due to biological factors (such as tumor progression or regression) or are due to differences in the images taken from the same woman. For an accurate determination of density changes over time, it is important that the images be aligned, as illustrated in FIG. 3C. The systems, media, and methods described herein provide a solution to the problem described above by allowing alignment of different mammogram images regardless of the size or orientation of the breast in the image, the amount of breast compression, or the mammography machine used to image the breast tissue. The systems, media, and methods described herein also provide for improved treatment of breast disorders based on the aligned images.

Alignment

Figure 2:
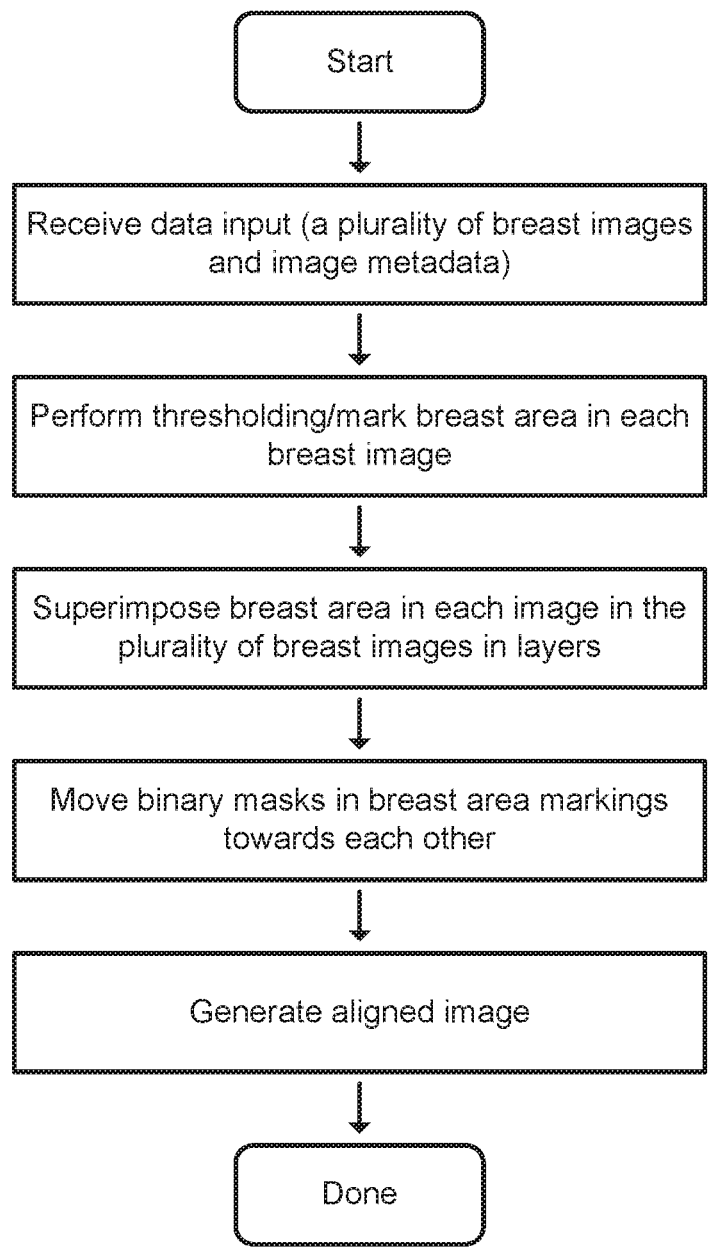
FIG. 2 shows a flowchart diagram of an exemplary alignment method described herein.

FIG. 2 shows a flow-chart diagram of one embodiment of the alignment method described herein. In one embodiment, the present disclosure provides computer-implemented methods comprising: (a) obtaining a data input comprising a plurality of breast images and image metadata of the subject; (b) applying an alignment algorithm to the plurality of breast images, the alignment algorithm further comprising (i) performing a thresholding method on the plurality of breast images marking breast area in the plurality of breast images; (ii) superimposing the breast area in each of the plurality of breast images in layers; (iii) moving binary masks in breast area markings towards each other to an optimal position of alignment of the breast areas where the pixel intensities of the breast images show minimal difference relative to one another; and (iv) generating an output aligned image comprising an area of mutual image information. In some embodiments, the method is fully automated.

Portions of the input breast image (e.g., the originally captured mammogram image or a scaled or normalized version of the breast image) as either breast area or background (based at least in part on the polynomial fit to a corresponding region of one or more of the kernel images to generate a binary image. For example, each pixel (or voxel) in the input breast image may be labeled as breast area or background based on a polynomial fit to a corresponding region of one or more of the kernel images. In this regard, if a corresponding region of a kernel image is fit with a polynomial satisfying a threshold order (e.g., order 3 or higher), the portion of the breast image may be labeled as breast area. If, however, none of the kernel images have a corresponding region that has been fitted with a polynomial satisfying the threshold order, the portion of the beast image may be labeled as background. White portion of the image will be labeled breast area and the dark portion will be the background.

In some embodiments, the method further comprises extracting texture features from the area of mutual image information in the aligned image. In some embodiments, the features are extracted by applying a cycle of thresholding methods to the aligned image and at least one edge tracing method. In some embodiments, the extraction further comprises stratification of the features into feature variables. In some embodiments, the extraction further comprises applying (a) a cycle of thresholding methods to the aligned image and at least one edge tracing method; and (b) stratification of the features into feature variables.

Suitable thresholding methods for texture feature extraction (feature measurement) include Otsu, RenyiEntropy, Huang, Intermodes, IsoData, Li, MaxEntropy, Mean, MinError, Minimum, Moments, Percentile, Shanbhag, Triangle, Yen. Suitable edge tracing method includes Skeletonize. Accordingly, in some embodiments, the cycle of thresholding method and edge tracing method comprises Otsu, RenyiEntropy, Huang, Intermodes, IsoData, Li, MaxEntropy, Mean, MinError, Minimum, Moments, Percentile, Shanbhag, Triangle, Yen and Skeletonize.

Suitable features useful for the purpose of the present invention include area, min, mean, max, std, modal, centroid, center, perimeter, bounding, fit, shape, integrated, median, skewness, kurtosis, limit, round, solidity, area_fraction. Accordingly, in some embodiments, the features measured by the cycle of thresholding methods and edge tracing method comprise area, min, mean, max, std, modal, centroid, center, perimeter, bounding, fit, shape, integrated, median, skewness, kurtosis, limit, round, solidity, area fraction.

In some of the embodiments, the stratification of features is performed by the size of the textures in the breast area. In some of the embodiments, the features are stratified to form feature variables. In other embodiments, the features are stratified and compiled into a row of feature variables.

In some embodiment, extraction and stratification of texture features and compiling into feature variables is performed on the plurality of breast images before the alignment of the plurality of the breast images.

In an aspect, the extraction and stratification further comprises obtaining additional input data such as breast image metadata tags and/or machine acquisition parameters (individually and collectively referred to as "image metadata" hereinafter). In some embodiments, the image metadata include, by way of non-limiting examples, x-ray exposure used (e.g., x-ray tube voltage of the machine, kilo volts and tube currents), compression force on breast and the thickness of compressed breast, mammograph machine type, machine specific thickness compression constants. In some embodiments, these image metadata are added and compiled into a single row of feature variables.

Breast Compression

In an aspect, the present invention provides that the computer-implemented method further comprises applying a breast compression score algorithm on the plurality of images based on the data input comprising a plurality of breast images and image metadata to generate a breast compression score. In some embodiments, the computer-implemented method comprises: (a) obtaining data input comprising image metadata reported breast compression force, the reported thickness of the compressed breast, the reported x-ray tube voltage of the machine, the mammography machine type, machine specific breast thickness compression constants; (ii) applying a breast compression score algorithm on the plurality of images based on the data input comprising image metadata to generate a breast compression score.

In some embodiments, the breast compression score algorithm is applied to the mutual information area in the plurality of images. In other embodiments, the breast compression score algorithm is applied to the breast area markings in the plurality of breast images. In yet other embodiments, the breast compress score algorithm is applied to mutual information area in the aligned images.

It will be appreciated by one of skill in the art that such methods are capable of processing a plurality of breast images to generate the breast compression score for each image, serially and simultaneously, in the plurality of breast images. In some embodiments, image metadata suitable for the purpose of the present invention includes, without limitation, one or more metadata such as reported breast compression force, the reported thickness of the compressed breast, the reported x-ray tube voltage of the machine, the mammography machine type, and machine specific breast thickness compression constants.

In some embodiments, the breast compression score is an image feature used for density measurement. The breast compressions score can be compared with the breast compression score
 determined by machine learning and incorporated into the statistical machine learning model used as comparator as described in the examples.

In some embodiments, the methods generate ≥500 feature variables, ≥600, ≥700, ≥800, ≥900, ≥1000 feature variables per mammogram. In some embodiments the systems, media, and methods generate up to 1027 feature variables per mammogram.

In some embodiments, the methods pre-process breast images prior to generating feature variables. Such pre-processing includes performing quality checks on the breast images, physically or digitally scaling breast images, normalizing images by pixel (or voxel) size, reorienting images, and the like.

Breast images may any suitable image of a breast of the subject. One of skill in the art will recognize that that there are multiple types of mammographic images, such as craniocaudal, containing a view of a breast as taken through the top of the breast, and mediolateral oblique, containing a view of a breast as taken from the center of the chest to the lateral of the breast. Additional supplemental views include mediolateral, lateromedial, lateromedial oblique, late mediolateral, step oblique, spot, spot compression, double spot compression, magnification, exaggerated craniocaudal—XCCL, and XCCM, axillary and the like.

The breast images may be obtained from various imaging modalities including an image projection on a single plane, overview images, rendered images (e.g., multi-planar reformatted images) or images derived from a series of spatially related or volumetric images, for example, tomosynthesis images. Images may be from any mammographic system vendor such as Phillips, General Electric (GE), Volpara, Sectra, Hologic, Siemens, and the like.

In some embodiments, the breast image is a DICOM formatted Full-Field Digital Mammographic (FFDM) image. In other embodiments, the breast image is an analog mammographic image. In still other embodiments, the breast images are 2D images, 3D images (such as tomosynthesis images), MRI image, CT-scan image, and the like. In yet other embodiments, the breast images are digital images, analog images, raw images, processed images, normalized images, or physically or digitally scaled images.

In other embodiments, the method further comprises generating a biomedical output. In yet other embodiments, the method further comprises diagnosing, predicting, or monitoring a breast disorder in a subject. In some embodiments, breast disorder is breast density masking or breast cancer.

In yet other embodiments, the method further designates a subject as a responder or non-responder to a therapy. In some embodiments, the therapy is a neo-adjuvant therapy adjuvant therapy comprising chemotherapy or endocrine therapy such as tamoxifen or aromatase inhibitors.

In yet other embodiments, the method further designates a treatment regimen for a subject diagnosed with a breast disorder or at risk of having a breast disorder. In some embodiments, the treatment regimen comprises an effective amount of low dose tamoxifen. In some embodiments, the low dose tamoxifen is 0.01 to 10 mg of low-dose tamoxifen.

In some embodiments, the low dose tamoxifen is 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg of tamoxifen per unit dose.

In another aspect of the present invention, the present disclosure provides a non-transitory computer-readable storage medium storing thereon executable instructions, that when executed by a computer, cause the computer to execute a method for aligning a plurality of breast images of a subject, the method comprising: (a) obtaining a data input comprising a plurality of breast images and image metadata; (b) applying an alignment algorithm to the plurality of breast images, the alignment algorithm comprising: (i) performing a thresholding method on the plurality of breast images marking breast area in the plurality of breast images; (ii) superimposing the breast area in each of the plurality of breast images in layers; (iii) moving binary masks in breast area markings towards each other to an optimal position of alignment of the breast areas where the pixel intensities of the plurality of breast images show minimal difference relative to one another; and (iv) generating an output aligned image comprising an area of mutual image information. In some embodiments, the method further comprises extracting texture features from the area of mutual image information in the aligned image. In other embodiments, the method further comprises generating a breast compression score from the area of mutual image information in the aligned image.

Portions of the input breast image (e.g., the originally captured mammographic image or a physically or digitally scaled or normalized version of the breast image) as either breast area or background (based at least in part on the polynomial fit to a corresponding region of one or more of the kernel images to generate a binary image. For example, each pixel (or voxel) in the input breast image may be labeled as breast area or background based on a polynomial fit to a corresponding region of one or more of the kernel images. In this regard, if a corresponding region of a kernel image is fit with a polynomial satisfying a threshold order (e.g., order 3 or higher), the portion of the breast image may be labeled as breast area. If, however, none of the kernel images have a corresponding region that has been fitted with a polynomial satisfying the threshold order, the portion of the beast image may be labeled as background. White portion of the image will be labeled breast area and the dark portion will be the background.

In some embodiments, the features are extracted by applying a cycle of thresholding methods to the aligned image and at least one edge tracing method. In some embodiments, the extraction further comprises stratification of the features into feature variables. In some embodiments, the extraction further comprises applying (a) a cycle of thresholding methods to the aligned image and at least one edge tracing method; and (b) stratification of the features into feature variables.

Suitable thresholding methods for texture feature extraction (feature measurement) include Otsu, RenyiEntropy, Huang, Intermodes, IsoData, Li, MaxEntropy, Mean, MinError, Minimum, Moments, Percentile, Shanbhag, Triangle, Yen. Suitable edge tracing method includes Skeletonize. Accordingly, in some embodiments, the cycle of thresholding method and edge tracing method comprises Otsu, RenyiEntropy, Huang, Intermodes, IsoData, Li, MaxEntropy, Mean, MinError, Minimum, Moments, Percentile, Shanbhag, Triangle, Yen and Skeletonize.

Suitable features useful for the purpose of the present invention include area, min, mean, max, std, modal, centroid, center, perimeter, bounding, fit, shape, integrated, median, skewness, kurtosis, limit, round, solidity, area_fraction. Accordingly, in some embodiments, the features measured by the cycle of thresholding methods and edge tracing method comprise area, min, mean, max, std, modal, centroid, center, perimeter, bounding, fit, shape, integrated, median, skewness, kurtosis, limit, round, solidity, area_fraction.

In some of the embodiments, the stratification of features is performed by the size of the textures in the breast area. In some of the embodiments, the features are stratified to form feature variables. In other embodiments, the features are stratified and compiled into a row of feature variables.

In some embodiments, the non-transitory computer-readable storage media comprising methods disclosed herein further comprise obtaining a plurality of breast images and breast image metadata of a subject. In some embodiments, the breast image metadata include, by way of non-limiting examples, reported x-ray exposure used (e.g., tube voltage, kilo volts and tube currents), reported compression force on breast and the reported thickness of breast during compression, reported mammography type, and reported machine specific breast thickness compression constants. In some embodiments, the non-transitory computer-readable storage media comprising methods disclosed herein further comprise applying a breast compression score algorithm on the plurality of images based on the breast image metadata to generate a breast compression score.

In at least one embodiment, the present disclosure provides a non-transitory computer-readable medium storing thereon executable instruction, that when executed by a computer, cause the computer to execute a method for computing a breast compression score comprising: (i) obtaining data input comprising image metadata; and (ii) applying a breast compression score algorithm on the plurality of images based on the data input comprising image metadata generating a breast compression score.

In some embodiments, these additional input data (such as image metadata) are added and compiled into a single row of feature variables.

In some embodiments, the non-transitory computer-readable storage media comprising methods disclosed herein generate ≥500 feature variables, ≥600, ≥700, ≥800, ≥900, ≥1000 feature variables per mammogram. In some embodiments, the non-transitory computer-readable media comprising the methods disclosed herein generate up to 1027 feature variables per mammogram.

In some embodiments, the non-transitory computer-readable media comprising methods pre-process breast images prior to generating feature variables. Such pre-processing includes performing quality checks on the breast images, physically or digitally scaling breast images, normalizing images by pixel (or voxel) size, reorienting images, and the like.

In some embodiments, the non-transitory computer-readable storage media comprising methods further comprises determining density measures from the area of mutual image information of the plurality of breast images and aligned images.

In other embodiments, the non-transitory computer-readable storage media comprising methods further comprises generating a biomedical output. In yet other embodiments, the non-transitory computer-readable storage media comprising methods further comprises diagnosing, predicting, or monitoring a breast disorder in a subject. In some embodiments, breast disorder is breast density masking or breast cancer.

In yet other embodiments, the non-transitory computer-readable storage media comprising methods further comprises designating a subject as a responder or non-responder to a therapy. In some embodiments, the therapy is a neo-adjuvant therapy, or adjuvant therapy comprising chemotherapy or endocrine therapy such as tamoxifen or aromatase inhibitors.

In yet other embodiments, the non-transitory computer-readable storage media comprising methods further comprises designating a treatment regimen for a subject diagnosed with a breast disorder or at risk of having a breast disorder. In some embodiments, the treatment regimen comprises an effective amount of low dose tamoxifen. In some embodiments, the low dose tamoxifen is 0.01 mg to 10 mg per unit dose. In some embodiments, the low dose tamoxifen is 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg of tamoxifen per unit dose.

In another aspect, the present disclosure provides a computer-implemented method for diagnosing, predicting, or monitoring a breast disorder in a subject, the method comprising: (a) obtaining a data input comprising a plurality of breast images and image metadata; (b) applying an alignment algorithm to the plurality of breast images, the alignment algorithm comprising: (i) performing a thresholding method on the plurality of breast images marking breast area in the plurality of breast images; (ii) superimposing the breast area in each of the plurality of breast images in layers; (iii) moving binary masks in breast area markings towards each other to an optimal position of alignment where the pixel intensities of each of the breast images of the plurality of breast images show minimal difference relative to one another; and (iv) generating an aligned image comprising an area of mutual image information; (d) determining case-specific density measures in the area of mutual image information based on a statistical machine learning model.

In some embodiments, computer-implemented method for diagnosing, predicting, or monitoring a breast disorder in a subject further comprises applying a breast compression score generating algorithm to the plurality of breast images for the generation of a breast compression score as disclosed herein.

In certain embodiments, the breast cancer is an invasive cancer or an in situ breast cancer.

In some embodiments, the breast cancer can be DCIS, LCIS, ILC, IDC, MIC, inflammatory breast cancer, ER-positive (ER+) breast cancer, HER2+ breast cancer, adenoid cystic (adenocystic) carcinoma, low-grade adenosquamatous carcinoma, medullary carcinoma, mucinous (or colloid) carcinoma, papillary carcinoma, tubular carcinoma, metaplastic carcinoma, or micropapillary carcinoma. In at least one embodiment, a single breast cancer tumor may be a combination of the foregoing or be a mixture of invasive and in situ cancer.

In some embodiments, the breast disorder is increased breast density. For example, the breast disorder is a BIRADs class C or class D breast density (beast density masking). In some embodiments, subjects have increased mammographic breast density classified as class C or class D breast density.

The present disclosure provides a computer-implemented method for determining a change in density measures in a subject's breast, the method comprising (a) generating a first aligned image and a second aligned image of the subject's breast; and (b) comparing average density measures from the area of mutual image information of the second aligned image relative to average density measures from the area of mutual image information of the first aligned image. In some embodiments, the first aligned image is from subject's right breast and the second aligned image is from the subject's left breast. In other embodiments, the first aligned image of a subject's breast is from a reference year (for example subject's first or an earlier breast scan for imaging) and the second aligned image is an aligned image from a later (target) year of that same breast of the subject. Thus, the present invention advantageously provides methods for detecting changes in the breast density in each of the two (right and left) breasts of the subject relative to the other breast as well as monitoring changes in breast over time.

The present disclosure provides a computer-implemented method for determining a change in density measures in a subject's breast, the method comprising: (a) obtaining a data input comprising (i) a plurality of breast images and image metadata from a reference year, and (i) a plurality of breast images and metadata from a target year; (b) applying an alignment algorithm to the plurality of breast images (from the reference year and the target year), the alignment algorithm comprising: (i) performing a thresholding method on the plurality of breast images (from the reference year and the target year) marking breast area in the plurality of breast images (from the reference year and the target year); (ii) superimposing the breast area in each of the plurality of breast images (from the reference year and the target year) in layers; (iii) moving binary masks in breast area markings towards each other to an optimal position of alignment where the pixel intensities of the breast images show minimal difference relative to one another; and (iv) generating an aligned image comprising an area of mutual image information; (c) determining density measures in the areas of mutual image information in the plurality of breast images (from the reference year and the target year) based on comparison with one or more of reference density measures or prediction datasets or statistical machine learning model; and (d) generating a biomedical output.

In some embodiments, computer-implemented method for determining a change in the density measures in a subject's breast further comprises applying a breast compression score generating algorithm to the plurality of breast images for the generation of a breast compression score as disclosed herein.

The present disclosure provides a non-transitory computer-readable storage medium storing thereon executable instructions, that when executed by a computer, cause the computer to execute a method for diagnosing, predicting, or monitoring a breast disorder in a subject, the method comprising: (a) obtaining a data input comprising a plurality of breast images and image metadata; (b) applying an alignment algorithm to the plurality of breast images, the alignment algorithm comprising: (i) performing a thresholding method on the plurality of breast images marking breast area in the plurality of breast images; (ii) superimposing the breast area in each of the plurality of breast images in layers; (iii) moving binary masks in breast area markings towards each other to an optimal position of alignment of the breast areas of each of the plurality of breast image where the pixel intensities of the breast images show minimal difference relative to one another; and (iv) generating an aligned image comprising an area of mutual image information; (c) determining case-specific density measures in the area of mutual image information based on comparison with one or more of reference density measures or reference prediction datasets or a statistical machine learning model.

Portions of the input breast image (e.g., the originally captured mammogram image or a scaled or normalized version of the breast image) as either breast area or background (based at least in part on the polynomial fit to a corresponding region of one or more of the kernel images to generate a binary image. For example, each pixel (or voxel) in the input breast image may be labeled as breast area or background based on a polynomial fit to a corresponding region of one or more of the kernel images. In this regard, if a corresponding region of a kernel image is fit with a polynomial satisfying a threshold order (e.g., order 3 or higher), the portion of the breast image may be labeled as breast area. If, however, none of the kernel images have a corresponding region that has been fitted with a polynomial satisfying the threshold order, the portion of the beast image may be labeled as background. White portion of the image will be labeled breast area and the dark portion will be the background.

In some embodiments, the method further comprises extracting texture features from the area of mutual image information in the aligned image. In some embodiments, the features are extracted by applying a cycle of thresholding methods to the aligned image and at least one edge tracing method. In some embodiments, the extraction further comprises stratification of the features into feature variables. In some embodiments, the extraction further comprises applying (a) a cycle of thresholding methods to the aligned image and at least one edge tracing method; and (b) stratification of the features into feature variables.

Suitable thresholding methods for texture feature extraction (feature measurement) include Otsu, RenyiEntropy, Huang, Intermodes, IsoData, Li, MaxEntropy, Mean, MinError, Minimum, Moments, Percentile, Shanbhag, Triangle, Yen. Suitable edge tracing method includes Skeletonize. Accordingly, in some embodiments, the cycle of thresholding method and edge tracing method comprises Otsu, RenyiEntropy, Huang, Intermodes, IsoData, Li, MaxEntropy, Mean, MinError, Minimum, Moments, Percentile, Shanbhag, Triangle, Yen and Skeletonize.

Suitable features useful for the purpose of the present invention include area, min, mean, max, std, modal, centroid, center, perimeter, bounding, fit, shape, integrated, median, skewness, kurtosis, limit, round, solidity, area_fraction. Accordingly, in some embodiments, the features measured by the cycle of thresholding methods and edge tracing method comprise area, min, mean, max, std, modal, centroid, center, perimeter, bounding, fit, shape, integrated, median, skewness, kurtosis, limit, round, solidity, area_fraction.

In some of the embodiments, the stratification of features is performed by the size of the textures in the breast area. In some of the embodiments, the features are stratified to form feature variables. In other embodiments, the features are stratified and compiled into a row of feature variables.

In some embodiment, extraction and stratification of texture features and compiling into feature variables is performed on the plurality of breast images before the alignment of the plurality of the breast images.

In some embodiments, the non-transitory computer-readable storage medium further comprises obtaining additional input data such as breast image metadata. In some embodiments, the image metadata include, by way of non-limiting examples, x-ray exposure used (e.g., kilo volts and tube currents), compression force on breast and the thickness of breast during compression. In some embodiments, these additional input data are added and compiled into a single row of feature variables.

In some embodiments, the non-transitory computer-readable medium further comprises generating ≥500 feature variables, ≥600, ≥700, ≥800, ≥900, ≥1000 feature variables per mammogram. In some embodiments the systems, media, and methods generate up to 1027 feature variables per mammogram.

In some embodiments, the methods pre-process breast images prior to generating feature variables. Such pre-processing includes performing quality checks on the breast images, physically or digitally scaling breast images, normalizing images by pixel (or voxel) size, reorienting images, and the like.

In some embodiments, non-transitory computer-readable storage medium storing thereon executable instructions, that when executed by a computer, cause the computer to execute a method for diagnosing, predicting, or monitoring a breast disorder in a subject, the method further comprises applying a breast compression score generating algorithm to the plurality of breast images for the generation of a breast compression score as disclosed herein. It will be appreciated by one of skill in the art that such methods are capable of processing a plurality of breast images to generate the breast compression score for each image serially and simultaneously in the plurality of breast images.

In some embodiments, image metadata suitable for the purpose of the present invention comprises, one or more image metadata such as reported breast compression force, reported thickness of the compressed breast, reported x-ray tube voltage of the machine, mammography machine type, and machine specific breast thickness compression constants, or a combination thereof.

Breast images may be any suitable image of a breast of the subject. One of skill in the art will recognize that that there are multiple types of mammographic images, such as craniocaudal, containing a view of a breast as taken through the top of the breast, and mediolateral oblique, containing a view of a breast as taken from the center of the chest to the lateral of the breast. Additional supplemental views include mediolateral, lateromedial, lateromedial oblique, late mediolateral, step oblique, spot, spot compression, double spot compression, magnification, exaggerated craniocaudal—XCCL, and XCCM, axillary and the like.

The breast images and image metadata may be obtained from various imaging modalities including an image projection on a single plane, overview images, rendered images (e.g., multi-planar reformatted images) or images derived from a series of spatially related or volumetric images, for example, tomosynthesis images. Images may be from any mammographic system vendor such as Phillips, General Electric (GE), Volpara, Sectra, Hologic, Siemens, and the like.

In some embodiments, the breast image is a DICOM formatted Full-Field Digital Mammographic (FFDM) image. In other embodiments, the breast image is an analog mammographic image. In still other embodiments, the breast images are 2D images, 3D images (such as tomosynthesis images), MRI image, CT-scan image, and the like. In yet other embodiments, the breast images are digital images, analog images, raw images, processed images, normalized images, or physically or digitally scaled images.

In another aspect, the present disclosure provides a non-transitory computer-readable storage media encoded with a computer program including instructions executable by a computer processing device comprising: (a) a software module configured to obtain input data comprising a plurality of breast images and image metadata of a subject; (b) a software module configured to apply an alignment algorithm comprising (i) performing a thresholding method on the plurality of breast images to mark breast area in the breast images; (ii) superimposing the breast area in each of the plurality of breast images in layers to form an aligned image of the subject's breast area; (iii) moving binary masks towards each other to an optimal position where their pixel intensities show minimal difference; and (iv) generating an aligned image comprising an area of mutual image information.

In some embodiments, the non-transitory computer-readable storage media further comprises one or more software modules configured for applying a breast compression score algorithm comprising: (i) obtaining a data input comprising a plurality of breast images and image metadata; (ii) applying a breast compression score algorithm on the data input. Application of the breast compression score algorithm generates a breast compression score. In some embodiments, the metadata can be one or more of ported breast compression force, the reported thickness of the compressed breast, the reported x-ray tube voltage of the machine, the mammography machine type, and machine specific breast thickness compression constants, or a combination thereof.

In some embodiments, the non-transitory computer-readable storage media further comprises one or more software modules configured to determine average density measures from the area of mutual image information comprising a breast compression score.

In other embodiments, the non-transitory computer-readable storage media further comprises one or more software modules configured to generate a biomedical output. In yet other embodiments, the application further comprises one or more software modules configured to diagnose, predict, or monitor a breast disorder in a subject. In some embodiments, breast disorder is breast density masking or breast cancer or a combination thereof.

In yet other embodiments, the non-transitory computer-readable storage media further comprises one or more software modules configured to designate a subject as a responder or non-responder to a therapy. In some embodiments, the therapy comprises neo-adjuvant or adjuvant chemotherapy or endocrine therapy such as tamoxifen or a combination thereof.

In yet other embodiments, the non-transitory computer-readable storage media further comprises one or more software modules configured to designate a treatment regimen for a subject diagnosed with a breast disorder or at risk of having a breast disorder. In some embodiments, the treatment regimen comprises an effective amount of low dose tamoxifen. In some embodiments, the treatment regimen comprises 0.01 mg to 10 mg of low dose tamoxifen In some embodiments, the low dose tamoxifen is 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 9 mg, 9.5 mg, or 10 mg of tamoxifen per unit dose.

In another aspect of the present invention, the present disclosure provides a computer-implemented system, comprising: (a) a digital processing device/processor comprising an operating system configured to perform executable instructions, and a memory device; (b) a computer program including instructions executable by a digital processing device comprising (i) a software module configured to receive a plurality of mammographic images of a subject and image metadata; (ii) a software module configured to apply alignment algorithm to the plurality of images, the alignment algorithm comprising (1) performing a thresholding method on the plurality of breast images to mark breast area in the breast images; (2) superimposing the breast area in each of the plurality of breast images in layers to form an aligned image of the subject's breast area; (3) moving binary masks towards each other to an optimal position where their pixel intensities show minimal difference; and (4) generating an output aligned image comprising an area of mutual image information; and (iii) a software module configured to analyze changes in breast density of a subject over time.

In some embodiments, the system further comprises one or more software modules configured for applying a breast compression score algorithm comprising: (i) obtaining data input comprising a plurality of breast images and image metadata; (ii) applying a breast compression score algorithm on the data input. Application of the breast compression score algorithm generates a breast compression score. In some embodiments, the metadata can comprise one or more of: ported breast compression force, the reported thickness of the compressed breast, the reported x-ray tube voltage of the machine, the mammography machine type, and machine specific breast thickness compression constants, or a combination thereof.

In some embodiments, the system further comprises one or more software modules configured to generate a biomedical output. In yet other embodiments, the system further comprises one or more software modules configured to diagnose, predict, or monitor a breast disorder in a subject. In some embodiments, breast disorder is breast density masking or breast cancer.

In yet other embodiments, the system further comprises one or more software modules configured to designate a subject as a responder or non-responder to a therapy. In some embodiments, the therapy comprises neo-adjuvant or adjuvant chemotherapy and/or endocrine therapy such as tamoxifen.

In yet other embodiments, the system further comprises one or more software modules configured to designate a treatment regimen for a subject diagnosed with a breast disorder or at risk of having a breast disorder. In some embodiments, the treatment regimen comprises an effective amount of low dose tamoxifen. In some embodiments, the treatment regimen comprises 0.01 mg to 10 mg of low dose tamoxifen. In some embodiments, the low dose tamoxifen is 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 9 mg, 9.5 mg, and 10 mg of tamoxifen per unit dose.

Biomedical Output

In some embodiments, the systems, media and methods disclosed herein comprise one or more biomedical outputs or uses thereof. In some embodiments, the biomedical output comprises one or more case-specific density measures. In some embodiments, the case-specific density measures include, by way of non-limiting examples, percent density, dense area, non-dense area, breast area, area of mutual image, breast compression score, and image metadata header. In some embodiments, the biomedical output comprises a nomogram for clinical presentation of density change in response to treatment. In other embodiments, the biomedical input comprises aligned breast images of a subject.

In some embodiments, the one or more case-specific density measures are determined by comparison to one or more prediction datasets. Prediction dataset were generated as disclosed herein by the systems, media, and methods of the present invention comprising matching and correlating the image analysis feature variables generated by the systems, media, and methods disclosed herein (R-dataset) with the (raw) image reference density measures and subjecting the feature variables to scaled principal component analysis (PCA).

In some embodiments, the comparison of the density measures of a case-specific output to one or more prediction datasets or reference density measures is based on Spearman's rank coefficient analysis, Bland-Altman fit plot analysis, Levene's test, Student-t test, breast compression score or a combination thereof.

In at least one embodiment, the comparison of the density measures of a case-specific output to a statistical machine learning model such as described herein (Examples).

In some embodiments, the biomedical output comprises changes in one or more density measures over time. In some embodiments, density measures in a case-specific output of one year is compared to density measures in the case-specific output of a different year is based on Spearman's rank coefficient analysis, Bland-Altman fit plot analysis, Levene's test, Student-t test, breast compression score or a combination thereof.

In some embodiments, the biomedical output further comprises case-specific features. In some embodiments, the case-specific features are stratified.

In some embodiments, a biomedical output further comprises a diagnostic output, predictive output, or a prognostic output. In other embodiments, the diagnostic output comprises a change in the breast density in a subject. In some embodiments, the prognostic output comprises a likelihood of recurrence of the breast cancer in the subject or designation of the subject as a responder or a non-responder to therapy such as to neo-adjuvant or adjuvant therapy comprising of chemotherapy or endocrine therapy. In some embodiments, the predictive output comprises predicting a response of the subject to a therapeutic regimen.

Classifiers (Feature Variables)

Further disclosed herein in some embodiments are systems, media and methods for generating one or more feature variables. In some embodiments, the systems, media, and methods disclosed herein generate feature variables using computer-implemented methods comprising (a) obtaining a data input comprising a plurality of breast images and image metadata; (b) performing a thresholding method on the plurality of breast images marking breast areas in the plurality of breast images; (c) calculating a breast compression score based on data input; (d) extracting texture features from the breast areas by applying one or more cycles of thresholding methods to the plurality of image and at least one edge tracing method; (e) stratifying the features into feature variables. In some embodiments, the classifiers comprise breast compression score. In some embodiments, the computer-implemented method further comprises applying a breast compression score algorithm to the plurality of breast images based on image metadata to generate to breast density score.

In some embodiments, the feature variables are image properties generated by systems, media, and methods disclosed herein comprising (a) aligning a plurality of images to form an aligned image comprising an area of mutual image information; (b) obtaining data input from the plurality of images to calculate a breast compression score; (c) extracting texture features from the area of mutual image information. In some embodiments, the extraction further comprises applying (a) a cycle of thresholding methods to the aligned image and at least one edge tracing method; and (b) stratification of the features into feature variables. In some embodiments, the image property is breast compression score generated by applying a breast compression score algorithm to the plurality of breast images based on image metadata to generate to breast density score.

Suitable thresholding methods for texture feature extraction (feature measurement) include Otsu, RenyiEntropy, Huang, Intermodes, IsoData, Li, MaxEntropy, Mean, MinError, Minimum, Moments, Percentile, Shanbhag, Triangle, Yen. Suitable edge tracing method includes Skeletonize. Accordingly, in some embodiments, the cycle of thresholding method and edge tracing method comprises Otsu, RenyiEntropy, Huang, Intermodes, IsoData, Li, MaxEntropy, Mean, MinError, Minimum, Moments, Percentile, Shanbhag, Triangle, Yen and Skeletonize.

Suitable features useful for the purpose of the present invention include area, min, mean, max, std, modal, centroid, center, perimeter, bounding, fit, shape, integrated, median, skewness, kurtosis, limit, round, solidity, area_fraction. Accordingly, in some embodiments, the features measured by the cycle of thresholding methods and edge tracing method comprise area, min, mean, max, std, modal, centroid, center, perimeter, bounding, fit, shape, integrated, median, skewness, kurtosis, limit, round, solidity, area_fraction.

In some of the embodiments, the stratification of features is performed by the size of the textures in the breast area. In other embodiments, the features are compiled into a row of feature variables.

In some embodiments, the systems, media, and methods disclosed herein further comprise obtaining additional input data such as breast image metadata and/or machine acquisition parameters. In some embodiments, the machine acquisition parameters include, by way of non-limiting examples, x-ray exposure used (e.g., kilo volts and tube currents), compression force on breast and the thickness of breast during compression. In some embodiments, these additional input data are added and compiled into a single row of feature variables.

In some embodiments, the systems, media, and methods generate ≥500 feature variables, ≥600, ≥700, ≥800, ≥900, ≥1000 feature variables per mammogram. In some embodiments the systems, media, and methods generate up to 1027 feature variables per mammogram.

In some embodiments, the systems, media, and methods pre-process breast images prior to generating feature variables. Such pre-processing includes performing quality checks on the breast images, physically or digitally scaling breast images, normalizing images by pixel (or voxel) size, reorienting images, and the like.

In some embodiments, the system, media, and methods start by reading the input data comprising breast images. In some embodiments, the breast image is a DICOM formatted Full-Field Digital Mammographic (FFDM) image. In other embodiments, the breast image is an analog mammographic image. In still other embodiments, the breast images are 2D images, 3D images (such as tomosynthesis images), MRI image, CT-scan image, and the like. In yet other embodiments, the breast images are digital images, analog images, raw images, processed images, normalized images, or physically or digitally scaled images.

The systems, media, and methods are configured to read a single breast image at a time or a plurality of breast images at the same time. This may be done manually, or in batches or be fully automated. In some embodiments, the systems, media, and methods of the present invention are fully automated.

The systems, media, and methods perform quality control and scan images for artifacts. It is an aspect of the present invention that non-biological artifacts are removed from analyses by the methods disclosed herein. (1) The computer programs read the images. If an image is found to be of poor quality containing artifacts, the image is quality check marked with the artifact. (2) The images are digitally scaled to a normalized image resolution. In some embodiments this normalized size is 200-micron per pixel (or voxel) size. In some embodiments, the analog images are cropped to remove any framing around the actual mammogram area. (3) The computer program flips the images so that the breast chest wall always appears in the same side, for example, the chest wall always appears to the left-side in mammogram. (4) The computer program detects if the mammogram appears as a negative and then inverts the Look-Up Tables when the pixel intensity representation is reversed.

In some embodiments, the computer program retrieves image metadata such as information on reported breast compression force, reported thickness of the compressed breast, reported x-ray tube voltage of the machine, mammography machine type, and machine specific breast thickness compression constants on the plurality of images. A breast compression score is calculated based on the retrieved information.

In some embodiments, breast areas of each of beast images of the plurality of breast images are aligned after generating feature variables to identify or determine areas of mutual image information as disclosed herein. In some embodiments, the density measures in each area of mutual image information in each breast image (belonging to the plurality of breast images) are determined by comparison to prediction data before alignment. The density measures of each mutual image information in each breast image is averaged. In other embodiments, the density measures are determined on the area of mutual image information in the breast area of the aligned image. In other embodiments, the density measurement of each mutual image information in each breast image is used in separate.

Digital Processing Device

In some embodiments, the systems, media and methods described herein include a digital processing device or a use of the same. In further embodiments, the digital processing device includes can be one or more hardware central processing unit (CPU) or a processor that carry out the devices functions. Non-limiting examples of processors include microprocessors, digital signal processors, graphics processing units, and the like. In still further embodiments, the digital processing device further comprises an operating system configured to perform executable instructions. In still other embodiments, the digital processing devices includes processors such as microprocessors, digital signal processors, graphics processing units, and data acquisition units. In some embodiments, the digital processing device is optionally connected to a computer network. In further embodiments, digital processing device is optionally connected to the Internet such that it accesses World Wide Web. In still further embodiments, the processor is optionally connected to a cloud computing infrastructure. In other embodiments, the digital processing device is optionally connected to Intranet. In other embodiments, the processor is optionally connected to a memory device or a data storage device.

In accordance with the description herein, suitable processors include, by way of non-limiting examples, server computers, desktop computers, laptop computers, notebook computers, sub-notebook computers, netbook computers, netpad computers, set-top computers, handheld computers, Internet appliances, Internet-of-things, mobile smartphones, tablet computers, personal digital assistants, videogame consoles, and vehicles. Those of skill in the art will recognize that many smartphones are suitable for use in the system described herein. Those of skill in the art will also recognize that television, video players, and digital music players with optional computer network connectivity are suitable for use in the system described herein. Suitable tablet computers include those with booklet, slate and convertible configurations, known to those of skill in the art.

In other embodiments, the digital processor device includes an operating system configured to perform executable instructions. The operating system is for example, software, including programs and data, which manages the device's hardware and provides services for execution of applications. Those of skill in the art will recognize that suitable server operating systems include by way of non-limiting examples, FreeBSD, OpenBSD, NetBSD®, Linux, Apple®, Mac OS X Server®, Oracle®, Solaris®, Windows Server®, VMware, and Novell Netware®. Those of skill in the art will recognize that suitable personal computer operating systems include, by way of non-limiting examples, Microsoft®, Windows®, Apple®, Mac OS X®, UNIX®, and Unix-like operating systems, such as GNU/Linux. In some embodiments, the operating system is provided by cloud computing. Those of skill in the art will also recognize that suitable mobile smart phone operating systems include, by way of non-limiting examples, Nokia Symbian OS®, Apple, iOS®, Research in Motion®, Blackberry OS®, Google® Android®, Microsoft Windows Phone OS®, Microsoft Windows Mobile OS®, Linux®, and Palm WebOS®.

In some embodiments, the device includes storage and/or memory device. The storage and/or memory device is one or more physical apparatuses used to store data or programs on a temporary or permanent basis. In some embodiments, the device is volatile memory and requires power to maintain stored information. In other embodiments the device is a non-volatile memory and retains stored information when the digital processing device is not powered. In further embodiments, the non-volatile memory comprises flash memory. In other embodiments, the non-volatile memory comprises dynamic random-access memory (DRAM). In yet other embodiments, the non-volatile memory comprises ferroelectric random-access memory (FRAM). In still other embodiments, the non-volatile memory comprises phase-change random-access memory (PRAM). In other embodiments, the device is a storage device including, by way of non-limiting examples, CD-ROMs, DVDs, flash memory drives, magnetic tape drives, magnetic disk drives, optical disc drives, solid-state drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In other embodiments, the display is a liquid crystal display (LCD). In further embodiments, the display is a thin film transistor liquid crystal display (TFT-LCD). In other embodiments, the display is organic light-emitting diode (OLED). In various other embodiments, the OLED display is a passive-matrix OLED (PMOLED), or active-matrix OLED (AMOLED) display. In some embodiments, the display is a plasma display. In other embodiments, the display is a video projector. In further embodiments, the display is a combination of devices such as those disclosed herein.

In some embodiments, the digital processor device includes an input device to receive information from a user. In some embodiments, the user is a subject having a breast disorder such as breast density or breast cancer, medical professional, researcher, analyst, or a combination thereof. In some embodiments, the medical professional is a doctor, nurse, physician's assistant, pharmacist, medical consultant, or other hospital or medical professional. In some embodiments, the input device is a keyboard. In some embodiments, the input device is a pointing device, by way of non-limiting examples, a mouse, trackball, trackpad, joystick, game controller, or stylus. In other embodiments, the input device is a touch screen or multi-touch screen. In yet other embodiments, the input device is a microphone, to capture voice or sound inputs. In still other embodiments, the input device is a video camera to capture motion or visual input. In further embodiments, the input device is a combination of devices such as those disclosed herein.

Figure 1:
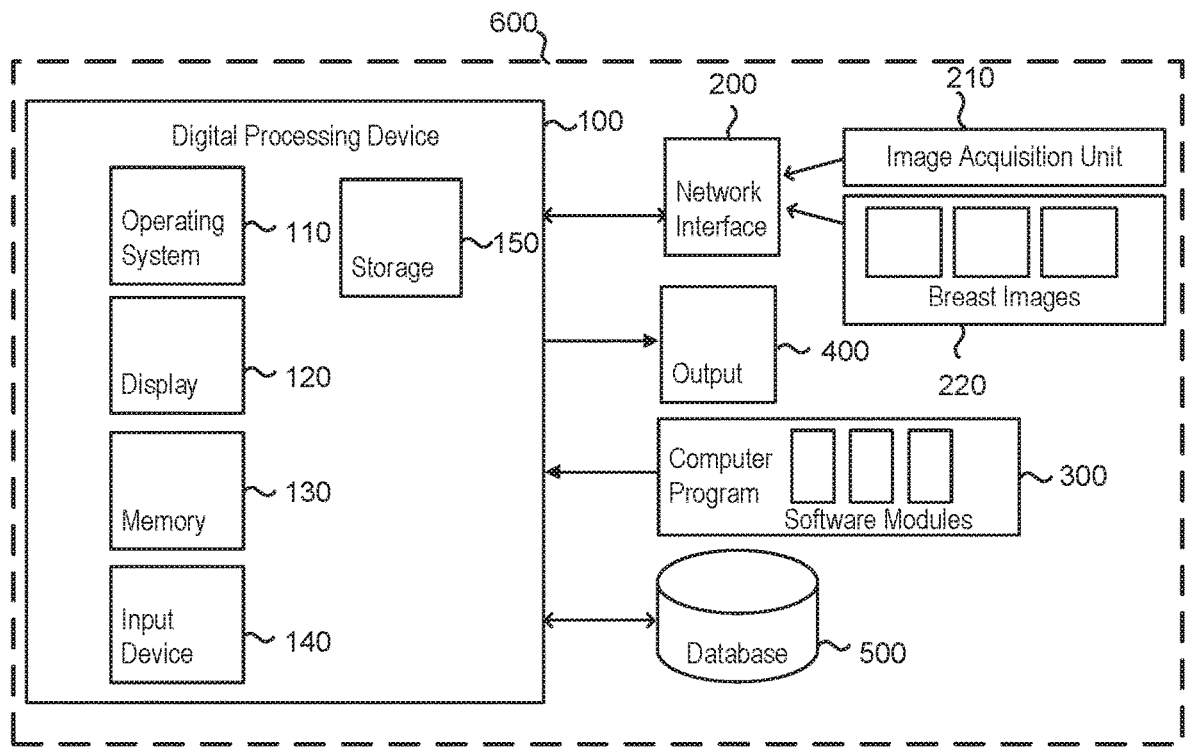
FIG. 1 is a block diagram of an exemplary computer-implemented system (600) that includes a digital processor device (100) configured with an operating system (110), a memory device (130), a storage device (150), a display (120) and an input device (140) such as a keyboard and a mouse for use by an operator of the system such as radiologist, and is configured to receive a plurality of breast images and image metadata from an image acquisition unit (210) such as a mammography system, an x-ray system, an MRI and the like, or from an image storage unit or device (220), directly or using a network interface. The digital processing device is configured to run computer programs (300) that comprise one or more software modules for alignment of the plurality of breast images, executing breast compressions score algorithms to generate breast compression score for the plurality of breast images using plurality of breast images and the image metadata. The digital processing device is also configured to generate an output (400) such as an aligned image of the subject's breast and/or a biomedical report that indicates changes in density measures of subject's breast (such as percent density, dense areas, non-dense area, breast area, breast compression score and mammogram header metadata) based on a plurality of breast images and image metadata acquired from the subject. The system is configured to have the digital processing unit store all input, breast images and output into a database (500).

FIG. 1. provides an exemplary computer-implemented system (600) that includes a digital processor device (100) configured with an operating system (110), a memory device (130), a storage device (150), a display (120) and an input device (140) such as a keyboard and a mouse for use by an operator of the system such as radiologist, and is configured to receive a plurality of breast images and image metadata from an image acquisition unit (210) such as a mammography system, an x-ray system, an MRI and the like, or from an image storage unit or device (220), directly or using a network interface. The digital processing device is configured to run computer programs (300) that comprise one or more software modules for alignment of the plurality of breast images, executing breast compressions score algorithms to generate breast compression score for the plurality of breast images using plurality of breast images and the image metadata. The digital processing device is also configured to generate an output (400) such as an aligned image of the subject's breast and/or a biomedical report that indicates changes in density measures of subject's breast (such as percent density, dense areas, non-dense area, breast area, breast compression score and mammogram header metadata) based on a plurality of breast images and image metadata acquired from the subject. The system is configured to have the digital processing unit store all input, breast images and output into a database (500).

Non-Transitory Computer-Readable Storage Medium

In some embodiments, the systems, media, and methods disclosed herein include one or more non-transitory computer-readable storage medium encoded with a program including instructions executable by the operating system of an optionally networked digital processing device. In further embodiments, the computer-readable storage medium is a tangible component of a digital processing device. In still further embodiments, the computer-readable medium is optionally removable from the digital processing device. In some embodiments, a computer-readable storage medium includes, by way of non-limiting examples, CD-ROMS, DVDs, flash memory drives, magnetic tape drives, magnetic disk drives, optical disc drives, solid-state drives, and cloud computing based systems, and services and the like. In further embodiments, programs and instructions are permanently, substantially permanently, semi-permanently, or non-transitorily encoded on the media. In still embodiments, programs and instructions are encoded on streaming media.

Computer Program

In some embodiments, the systems, media, and methods disclosed herein include at least one computer program, or use of the same. A computer program includes a sequence of instructions, executable in the digital processing device's compute, (such as a CPU or a microprocessor) written to perform a specified task. Computer-readable instructions may be implemented as a compute, program modules, such as function, objects, applications, Application Programming Interfaces (APIs), data structure, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one or more sequence of instructions. In other embodiments, a computer program comprises a plurality of sequences of instructions. In some embodiments, a computer program is provided from one location. In other embodiments, a computer program is provided from a plurality of locations. In various embodiments, the computer program includes one or more software modules. In various embodiments, a computer program includes, in part or in whole, one or more web applications, one or mobile applications, one or more standalone applications, one or more web browser plugins, extensions, add-ins, or combinations thereof.

Web Application

In some embodiments, a computer program includes a web application. In light of the disclosures provided herein, those of skill in the art will recognize that a web application, in various embodiments, utilizes one or more software frameworks and one or more database systems. In some embodiments, a web application is created upon a software frame work such as JAVA, Microsoft.NET or Ruby on Rails (RoR). In some embodiments, a web application utilizes one or more database systems, including, by way of non-limiting examples, relational, non-relational, object oriented, associative, and XML database systems. In further embodiments, suitable relational database systems include, by way of non-limiting examples, Microsoft® SQL Server, mySQL®, noSQL, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or extensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tel, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof [0080] Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code.

Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the systems, media, and methods disclosed herein include one or more databases, data sources, or use of the same. In view of the disclosure provided herein, those of skill in the art will recognize that many databases are suitable for storage and retrieval of cancer data. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

In some embodiments, the databases or data sources are selected from medical records, clinical notes, genomic databases, biomedical databases, clinical trial databases, scientific databases, or a combination thereof. In some embodiments, the one or more databases or sources comprise publicly available databases, proprietary databases, or a combination thereof.

Data Transmission

In some embodiments, the systems, media and methods disclosed herein further comprise transmission of the case-specific output, biomedical output, biomedical report, classifier or a combination thereof. In some embodiments, the outputs, reports, and/or classifiers are transmitted electronically. In some embodiments, the case-specific output, biomedical output, biomedical report and/or classifiers are transmitted via a web application. In some embodiments, the web application is implemented as software-as-a-service.

In some embodiments, the systems, media and methods disclosed herein further comprise one or more transmission devices comprising an output means for transmitting one or more data, results, outputs, information, biomedical outputs, biomedical reports and/or classifiers. In some embodiments, the output means takes any form which transmits the data, results, requests, and/or information and comprises a monitor, printed format, printer, computer, processor, memory location, or a combination thereof. In some embodiments, the transmission device comprises one or more processors, computers, and/or computer systems for transmitting information.

In some embodiments, transmission comprises tangible transmission media and/or carrier-wave transmission media. In some embodiments, tangible transmission media include coaxial cables; copper wire and fiber optics, including the wires that comprise a bus within a computer system. In some embodiments, carrier-wave transmission media takes the form of electric or electromagnetic signals, or acoustic or light waves such as those generated during radio frequency (RF) and infrared (IR) data communications.

In some embodiments, the outputs, reports, and/or classifiers are transmitted to one or more users. In some embodiments, the one or more users are a subject suffering from breast disorders such as breast density or breast cancer, medical professional, researcher, analyst, or a combination thereof. In some embodiments, the medical professional is a doctor, nurse, physician's assistant, pharmacist, medical consultant, or other hospital or medical personnel.

Exemplary Uses

In some embodiments, the systems, media and methods disclosed herein are useful not only for diagnosing, predicting or monitoring a status or outcome of a breast disorder such as breast density and breast cancer in a subject but also for predicting a response to a therapeutic regimen.

In as aspect, provided herein in certain embodiments, are patient populations for whom systems, media, and methods as well as the pharmaceutical compositions disclosed herein are particularly useful in reducing breast disorders, neo-adjuvant, adjuvant and preventive settings. Patients that benefit from adjuvant endocrine such as with tamoxifen therapy can be identified by the systems, media, and methods disclosed herein. Likewise, non-responders are also identified, and can advantageously selected for alternative treatments.

In the preventive setting density change has also been demonstrated to be a good marker of tamoxifen response. For more than 40 years, 20 mg of tamoxifen has been used in breast cancer patients to reduce the risk of recurrence. It has also been shown that 20 mg of tamoxifen reduces the risk of breast cancer in perfectly healthy women. However, tamoxifen treatment is associated with side-effects, which are similar to menopausal symptoms, and in rare cases endometrial cancer and thromboembolism (Mallick S, Benson R, Julka P K; Breast cancer prevention with anti-estrogens: review of the current evidence and future directions; Breast Cancer. 2016 March; 23(2):170-7). The side effects are probably one reason tamoxifen is not used in the preventive setting despite the substantial risk reducing effect. Factors that influence risk of breast cancer are known to influence density.

In an aspect, the present disclosure provides methods of treating subjects identified using the systems, media, and methods disclosed herein with a composition comprising tamoxifen or a salt thereof in a low dose ranging from 0.1 mg to 10 mg per unit dose. Compositions comprising tamoxifen or a salt thereof are administered to the subject at a unit dose of 0.1 mg, 0.5 mg, 1 mg, 2 mg 2.5 mg, 3 mg, 4 mg, 5 mg, 6 mg, 7 mg, 7.5 mg, 8 mg and 10 mg. The compositions may be administered once a day, twice, a day, thrice a day, four times a day, every other day, twice a week, weekly, fortnightly, twice a month, monthly, quarterly, once every six months, or annually. However, the particular mode of administration and the dosage regimen will be selected by the attending clinician, taking into account the particulars of the case (e.g., the subject, the disease, the disease state involved, and whether the treatment is preventive). Treatment may involve daily or multi-daily doses of compound(s) over a period of a few days to months, or even years.

Compositions comprising low dose tamoxifen and salts thereof can be prepared by methods known in the art. Several methods for the synthetic preparation of tamoxifen and salts thereof are known in the art (EP 0168175 A1; Miller et al. J. Org. Chem., 1985, 50 (12), pp 2121-2123; Maji et al. Int J Nanomedicine. 2014; 9:3107-3118.). In some embodiments, the compositions comprising endoxifen further comprises an excipient. Such an excipient can be compatible with the intended route of administration.

Compositions comprising low dose tamoxifen or a salt thereof may be administered to the subject orally, topically intraductally (into a breast milk duct), or parentally.

Compositions intended for oral use may be prepared in either solid or fluid unit dosage forms. In at least some embodiments, the compositions are formulated for oral delivery as tablets, caplets, capsules, pills, powders, troches, elixirs, suspensions, syrups, wafers, chewing gums, dragees, lozenges, and the like. The tablets, caplets, and capsules may be coated or uncoated by techniques known in the art to control or delay disintegration and absorption in the gastrointestinal tract and thereby provide a sustained action over a longer period of time. The tablet can be an enteric tablet, the caplet can be an enteric caplet, and the capsule can be an enteric capsule. In some embodiment, the capsule is a hard capsule or a soft capsule.

The present disclosure additionally provides for therapeutic kits containing one or more of the compositions comprising low dose tamoxifen or a salt thereof for use in the treatment of a subject having or at risk of having a breast disorder such as breast density and/or breast cancer. The contents of the kits can be lyophilized and the kit can additionally contain a suitable solvent for reconstitution of the lyophilized components. Individual components of the kit would be packaged in separate containers and associated with such containers would be a notice in the form prescribed by a governmental agency regulating the manufacture, use, or sale of the pharmaceutical products, which notice reflects the approval by the agency of manufacture for use or sale for subject's administration.

EXAMPLES

Example 1

Database Construction; Feature Classification
Dataset (KARMA)

In order to establish the largest possible pool of potential training cases for predictor building, mammographic images from 41,353 breast cancer free women were sampled from KARMA with available raw and processed images from the same mammograms (available from General Electrics, Philips, Sectra, Hologic, SIEMENS, FUJI, Agfa, Array Group, and Vidar).

Software Application

ImageJ programming framework, a Java based software, developed by National Institutes of Health (http://rsb.info.nih.gov/ij/index.html. Accessed 30 March, 2017) was modified to develop an aspect of the present invention, the computer program ("STRATUS" hereinafter).

Data Input

Raw and processed images from same mammogram of 41,353 women were used to analyzed and used to measure breast density using the FDA approved density measurement tool VuComp M-Vu tool. This served as the reference measure for learning and validation of the software application STRATUS. The same raw and processed images (input image) from above were then subject to analyses (feature extraction, learning and validation) by STRATUS.

STRATUS analyzed 1,027 image features of the processed and raw images from the same mammograms breast images. STRATUS processor (in an image processing device) started by reading data input comprising beast images, formatted full-field digital and analog mammograms (the DICOM (http://dicom.nema.org/. Accessed 30 March, 2017), and for the digital images, also image metadata including mammography machine acquisition parameters. The images were Full Field Digital Mammograms from digital vendors (General Electric, Sectra, Philips, Hologic, SIEMENS, FUJI, Agfa) and digitized analog vendors Array Corp. and Vidar.

Pre-Processing of Image

STRATUS pre-processed the images. Pre-processing included quality checking and removal of artifacts, digital scaling, normalization of pixel size, orienting images as necessary. The STRATUS quality checked the breast images and marked dubious breast images of questionable quality into output files. The images were scanned for artifacts and, if present, they were removed. Images were further normalized to 200-micron pixel size. Analog mammograms were physically scaled (e.g., cropped) to remove the framing around the actual mammogram area. STRATUS flipped the images so the breast chest wall always appeared to the left-hand side in mammogram. STRATUS detected pixel representation of the images and inverted the Look-Up-Table if the mammogram appeared as a negative (i.e. when the pixel intensity representation was reversed).

Breast Compression Score

STRATUS retrieved information from the meta data tags in the images for breast, machine acquisition parameters, compression force used during mammography, thickness of the compressed breast, and x-ray tube voltage, specific to each mammography machine type, (individually and collectively "image metadata") were programmed into STRATUS. A breast compression score was calculated based on this information by multiplying x-ray tube voltage with the compressed breast thickness.

Feature Classification

STRATUS subjected the breast images to thresholding methods and marked the breast areas. Thresholding methods, Intermodes, Triangle, or Means, were used depending on the quality of the image (analog, digital, raw, processed detected by STRATUS)

STRATUS identified and measured textures in the breast images to form the basis for measuring mammographic density. Textures of the breast image were extracted i.e., identified, by subjecting the images to a cycle of fifteen (15) thresholding methods (Otsu, RenyiEntropy, Huang, Intermodes, IsoData, Li, MaxEntropy, Mean, MinError, Minimum, Moments, Percentile, Shanbhag, Triangle, Yen) and an edge tracing method (Skeletonize). Twenty features (area, min, mean, max, std, modal, centroid, center, perimeter, bounding, fit, shape, integrated, median, skewness, kurtosis, limit, round, solidity, area_fraction) were measured for each cycle on (i) the whole segmented breast area and (ii) in the sub areas defined by the pixel size of the thresholded image particles.

Additional image features included in the feature classification were mammography machine acquisition parameters and other image metadata included in the mammogram headers. Such mammography acquisition parameters included the x-ray exposure used (kilo volt and tube current), the compression force and the thickness of the breast during compression.

All extracted image features are measured for each thresholding method and compiled in the that order into one row with up to 1,027 variables per mammogram.

Example 2

Predictor Building & Density Measurement

For predictor building for measuring density measures from a breast image and image metadata using machine learning, STRATUS, was configured to relate the 1,027 feature variables (including breast compression scores) from Example 1 to the raw image reference measures of density obtained using the FDA-approved VuComp M-Vu tool on the same mammograms.

The learning step used R programming framework developed by the r-project.org and ran as a program within the STRATUS programming framework. The STRATUS 1,027 image analysis variables from Example 1 were loaded as an R dataset. The (raw) image Reference Measures of breast density were matched to the corresponding processed 1,027 image features variables generated by STRATUS in Example 1. Scaled principal component analysis (PCA) was performed on the feature variables and a prediction dataset was created based on the PCA data.

STRATUS was configured to apply a transforming algorithm, square root transform, to the original image reference measures (percent density, dense area, breast area) (Solomon, S., R., & Sawilowsky, S. S. (2009). Impact of rank-based normalizing transformations on the accuracy of test scores. Journal of Modern Applied Statistical Methods, 8(2), 448-462). Application of the transforming algorithm transformed the reference measures to a distribution close to normal form.

The R package "penalized" was used to fit a generalized linear penalized lasso regression model. One hundred loops of model fits with ten-folded cross-validation were used to calculate the mean lambda used to penalize the estimates for the final model. This procedure was done for the density measures (percent density, dense area, and breast area).

The outcome density measures were then back transformed to original density distribution by powering the values with two. The accuracy of the measurements was tested in an independent validation dataset, FIG. 5. This two-step procedure with training and validation was performed for each type of mammogram and mammography machine using up to 4,000 mammograms per machine to generate the statistical machine learned algorithm ("Statistical machine learning model") that measures density. The statistical model measures density on any new mammograms from the same mammography machine vendors as the model was trained on and includes the breast compression score.

Post-Processing

The algorithm (statistical machine learning model) outputs records for each analyzed mammogram includes percent density in the breast, dense area, non-dense area, breast area, breast compression score, and mammogram header metadata.

Example 3

Alignment of Images

An alignment algorithm was developed and incorporated into STRATUS for aligning a plurality of breast images. The alignment tool can be a stand-alone computer program or an addition. The alignment of breast images provides for reduced non-biological variability between images over time as observed in FIG. 7.

Several techniques are available for aligning images (Thévenaz, U. E. Ruttimann, M. Unser, A Pyramid Approach to Subpixel Registration Based on Intensity, IEEE Transactions on Image Processing, vol. 7, no. 1, pp. 27-41, January 1998; US20160019690; US20150023576; US20060245629; US20090060300).

The translation registration method used herein preserved the largest part of the original image area and was used in the final analysis below (Example 4). The alignment protocol was developed to analyze several mammograms in a time series and to not be sensitive to the differences in pixel intensities, which can be seen between processed and raw or analogue images.

The alignment tool of STRATUS used the TurboReg plugin in ImageJ to read plurality of breast images (for example, pairs of Full Field Digital Mammograms) and to align the images. STRATUS applied the algorithm tool to a plurality of images to align the images. First, each breast area was marked using thresholding processes/methods, Intermodes, Triangle, or Means.

Choice of the thresholding method depends on the quality of the image (digital, analog, raw, processed and is detected by STRATUS).

Binary masks from the breast area markings (marks) were then used to guide the superimposition of the breast areas on top of each other in layers. For example, the breast area in a first image or a reference or source image was overlaid (superimposed) on the breast area in a second image or a target image. It is to be understood, that superimposition can also be performed by overlaying a target image on top of a reference or source image and is an embodiment of the present invention.

To align the images, the binary masks were moved towards each other to an optimal position where their pixel intensities reached minimal difference using least square means, a translation technique based on Marquardt-Levenberg algorithm (Levenberg, Kenneth (1944). "A Method for the Solution of Certain Non-Linear Problems in Least Squares". Quarterly of Applied Mathematics. 2: 164-168; Marquardt, Donald (1963). "An Algorithm for Least-Squares Estimation of Nonlinear Parameters". SIAM Journal on Applied Mathematics. 11 (2): 431-441). The positioning technique is therefore not sensitive to aligning images with differences in pixel intensities such as raw and processed mammograms. Thus, the alignment tool need not rely on differences of pixel intensity in the images. The actual breast area pixel information in the image is linked to the mask position and moved accordingly. The internal positioning of the pixels in the images was preserved (i.e. not distorted) during the move. Any parts of the images outside the mutual image information are cropped. Merged images or snap shots of the superimposed images before and after alignment using binary masks are saved, together with the moving coordinates, in an output file.

Post Processing

The density measurement of the aligned images was then performed in the order shown with above Examples 1 and 2.

Example 4

Three Swedish Datasets 70,877 women (the KARMA cohort) attended mammography screening between January 2011 to March 2013 at four mammography units in Sweden (Gabrielsson M et al.;

Cohort profile: The Karolinska Mammography Project for Risk Prediction of Breast Cancer (KARMA); International Journal of Epidemiology, 2017). Participants donated blood, answered a web-based questionnaire, and raw and processed digital mammograms were stored. Women reported length and weight, family history of breast cancer, age at menarche, parity, age at first child, menopausal status, and ever use of hormone replacement therapy (HRT). Breast cancer cases, invasive and in-situ, were identified through the Swedish Information Network for Cancer treatment (INCA) national breast cancer quality register.

The population based LIBRO1 study included invasive and in-situ breast cancer cases diagnosed between 2001 and 2008 in the Stockholm area. Frequency matching was used to age-match 2,443 breast cancer cases with the available controls from the KARMA study. The third Swedish study was the population based SASBAC study which included 1,194 women diagnosed with invasive and in-situ breast cancer between 1993-1995 and 1,086 controls density sampled and frequency matched on age (Li J et. al; High-throughput mammographic density measurement: a tool for risk prediction of breast cancer; Breast Cancer Research 2012, 14:R114). Pre-diagnostic analogue films were collected for all cases, and images closest to recruitment date were collected for the controls. The cases and controls in LIBRO1 and SASBAC also contributed with the same lifestyle factors from the same set of questions as was used in KARMA.

Density Measures

Density measure (percent density, dense area, and breast area) were measured as described in Examples 1 and 2. Density measures for analog images were developed with all the available women in the SABAC study (Li J et. al; High-throughput mammographic density measurement: a tool for risk prediction of breast cancer; Breast Cancer Research 2012, 14). The density measure was trained using the same algorithm as for digital images as described in Examples 1 and 2, by learning on one of the breasts and validating on the contralateral breast.

Risk Estimation and Discrimination

Using samples from the described datasets (KARMA, SABAC and LIBRO1), the association between the density measurements derived from different kind of images and breast cancer incidence was estimated. This was done to contrast cases and controls with different types of mammograms; contrasting cases with raw mammograms to controls with raw mammograms, processed cases to processed controls, processed to analogue, and analogue to analogue.

The first risk estimation was done on a nested case-control study sample with a two-year follow-up using the available 433 incident breast cancer cases age-matched in one-year bands with 1,732 controls in the KARMA study (Table 1). The risk association was estimated using density measures of the raw and processed mammograms in separate (contrasting raw cases to raw controls; processed cases to processed controls).

The second risk estimation set was defined as the 1,194 breast cancer cases in the LIBRO1 study possible to age-match in one-year bands with the available 1,086 controls from SASBAC (analogue cases to analogue controls).

The third risk estimation set was defined as the 2,443 LIBRO1 cases age-matched in one-year bands with the available 2,999 controls from the KARMA cohort (analogue cases to digital controls).

Alignment of Time Series Images

The problem with not aligning images becomes evident when looking at FIG. 3, frame A. Two images from the same woman have been superimposed on each other. Most of the breast was seen in the image in the bottom breast (showing a green border). In contrast, the top breast in the image (with the red border) lacks a large part of the breast and thereby also lacks a part of the dense area. The top breast area (outlined by a red contour) was 185 $cm^2$. The corresponding area was 197 $cm_2$ for the bottom breast (outlined by the green contour). The two images were then aligned using the alignment tool of the present invention as described in Example 3, and as a result of the alignment process, the two breast areas are now 185 cm2 (area of mutual image information) FIG. 3, frame B.

Two datasets were used to evaluate the alignment tool. First, for 11,409 of the KARMA participants, two mammograms were taken within minutes of each other which provided an opportunity to study differences in density measures that possibly could not be due to biological alterations. In this dataset, two images from the same visit were aligned to create an aligned image according to the process described in Example 3. Dense area was measured in the area of mutual image information in the aligned image using the alignment tool of STRATUS as described in Example 2).

Secondly, all KARMA participants that had been through two rounds of negative screens (N=55,073) were used to test if density measures of aligned images differed from the regular density measures. Dense area was measured in left or right breast at each screen and the average dense area was calculated using STRATUS as described in Examples 1 and 2.

Statistical Methods

The agreements between the STRATUS and reference density measures were investigated using Spearman's rank correlation coefficient and Bland-Altman fit plot (Spearman, C. (1907). "Demonstration of Formulae for True Measurement of Correlation". The American Journal of Psychology. 18 (2): 161-169. doi:10.2307/1412408; Bland J M, Altman D G (1999) Measuring agreement in method comparison studies. Stat Methods Med Res 8:135-160).

The differences between the mammographic density measures of different mammogram types (analog, digital, raw, processed) were investigated using least square means of mammographic percent density adjusted for age, BMI, and two mammography machine related factors; voltage of the x-ray tube and thickness of the compressed breast.

The association between mammographic density and breast cancer was estimated using conditional logistic regression in the three case-control study samples in separate and in all study samples combined. Three models where constructed to assess potential risk association confounders. The first model included percent density and age, the second model included BMI, percent density and age, and the full model the ever use of HRT, menopause status, and family history of breast cancer as well as percent density, age and BMI. The addition of x-ray tube voltage, breast thickness, and an indicator of study sample to the full model did not change the estimates and were therefore excluded in the final model. The odds-ratios were calculated per standard deviation with 95% Wald confidence intervals. The discrimination performances of the models were calculated with area under the receiver operating curve (AUC) and 95% Wald confidence intervals.

The alignment effect was calculated by first subtracting the last measure from the first for each alignment status. The density differences were further aggregated as means and standard deviations for aligned and non-aligned images in separate. The differences in standard deviations and means comparing the aligned and non-aligned images were tested using Levene's test (Levene, H. (1960). Robust tests for equality of variances. In Contributions to Probability and Statistics; Essays in Honor of Harold Hotelling, I. Olkin editor, 278-292. Stanford, California: Stanford University Press) and the Student's t-test (Student [William Sealy Gosset] (1908). The probable error of a mean. Biometrika, Volume VI, March, 1908, No. 1).

The longitudinal density analysis was performed by first calculating density change per year for aligned and non-aligned images in separate. The change in dense area per year was calculated by subtracting the last measure from the first and divide by the number of years between examinations. The mean and standard deviation of the density changes were calculated in the same way using the Student's t-test and the Levene's test. Yearly density changes by age and BMI were modelled using local polynomial regression and plotted.

All tests were two-sided with 5% significance level. All analyses were performed using the statistical software SAS v9.4.

Results

In total, 45,417 women from the KARMA, LIBRO1, and SASBAC studies contributed with raw and processed mammograms from nine different types of mammograms from six vendors (Table 1). The mammographic density risk association was estimated in three case—control study samples (Table 1).

TABLE 1

Description of the three case - control study samples used to calculate risk of breast cancer of mammographic density measured by STRATUS

| Characteristics by study sample | Cases | Controls |
| --- | --- | --- |
| KARMA study sample | | |
| Number of participants | 433[1] | 1,732[1] |
| Age (years), mean (SD) | 57.4 (9.2) | 57.4 (9.2) |
| Ever use of HRT, percent | 39 | 36 |
| Postmenopausal, percent | 65 | 65 |
| Family history of breast cancer, percent | 19 | 13 |
| LIBRO1/KARMA study sample | | |
| Number of participants | 2,443[2] | 2,999[1] |
| Age (years), mean (SD) | 60.8 (9.5) | 60.8 (9.5) |
| Ever use of HRT, percent | 53 | 34 |
| Postmenopausal, percent | 92 | 90 |
| Family history of breast cancer, percent | 20 | 13 |
| LIBRO1/SASBAC study sample | | |
| Number of participants | 1,194[2] | 1,086[2] |
| Age (years), mean (SD) | 63.1 (6.4) | 63.1 (6.4) |
| Ever use of HRT, percent | 54 | 50 |
| Postmenopausal, percent | 100 | 100 |
| Family history of breast cancer, percent | 15 | 8 |

Figure 5:
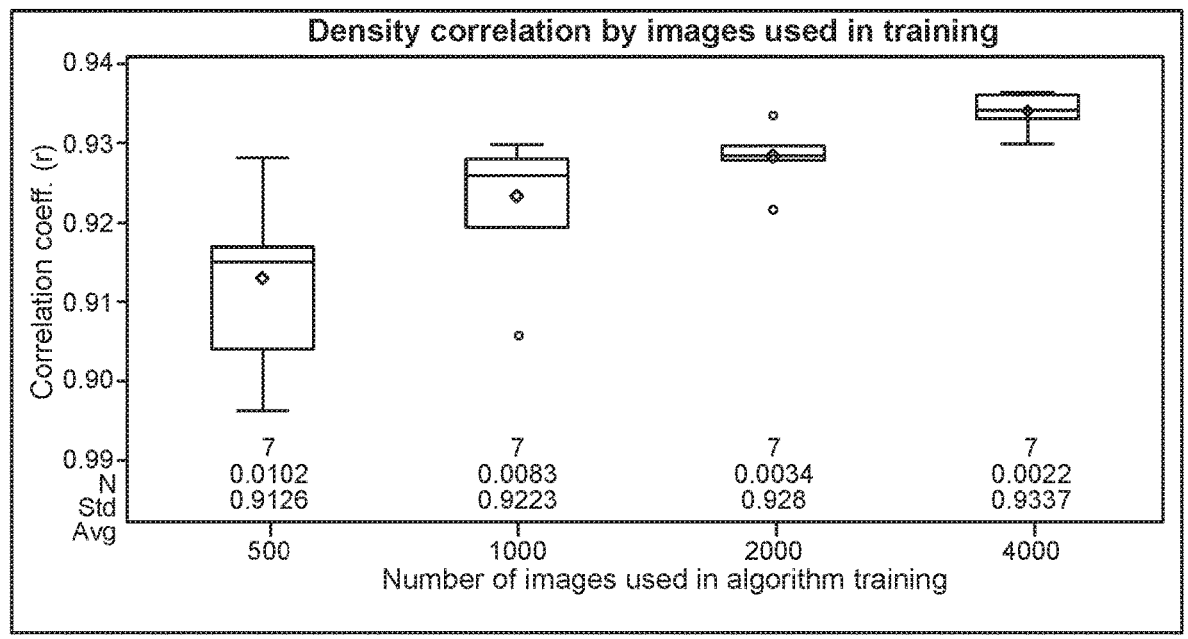
FIG. 5 shows a Spearman rank correlation r of percent density between raw and processed images per type of mammography machine in relation to the number of mammogram pairs used in the training dataset for machine learning of STRATUS. The figure shows results from the validation dataset.
Figure 6:
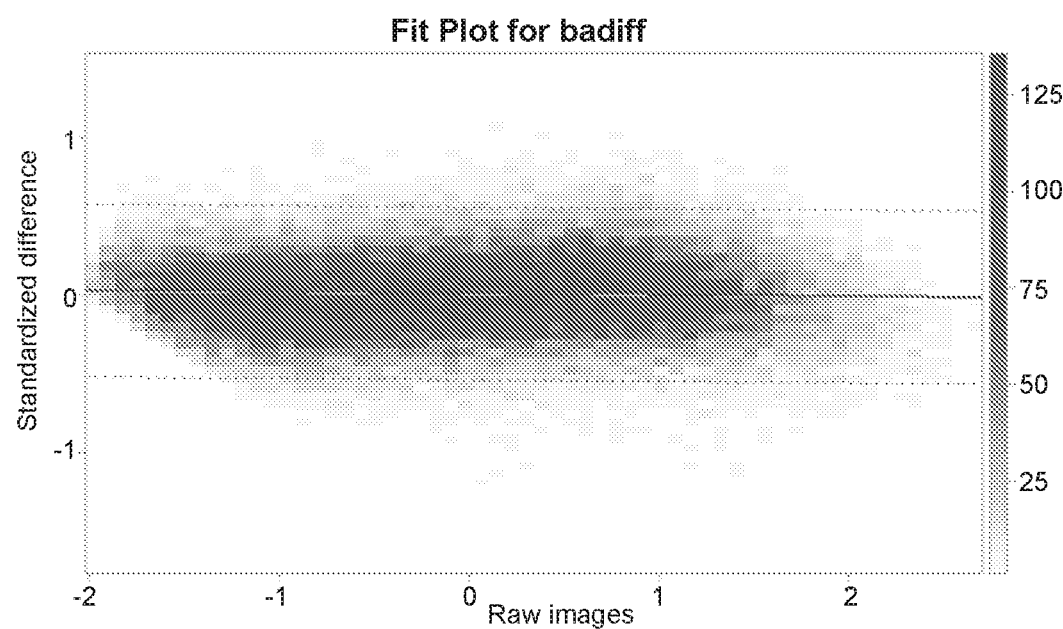
FIG. 6 shows a Bland-Altman fit plot with standardized percent density comparing the agreement with 95% CI (dotted lines) between raw and processed images in the validation dataset. The validation dataset included mammograms from all mammography machines trained with up to 4,000 mammograms. The graph was enhanced with red-to-white color transition to indicate the number of density measures in the plot (right-hand scale). The standardized mean density difference between the raw and processed mammograms was 0.01 with standard deviation 0.28.
Figure 7:
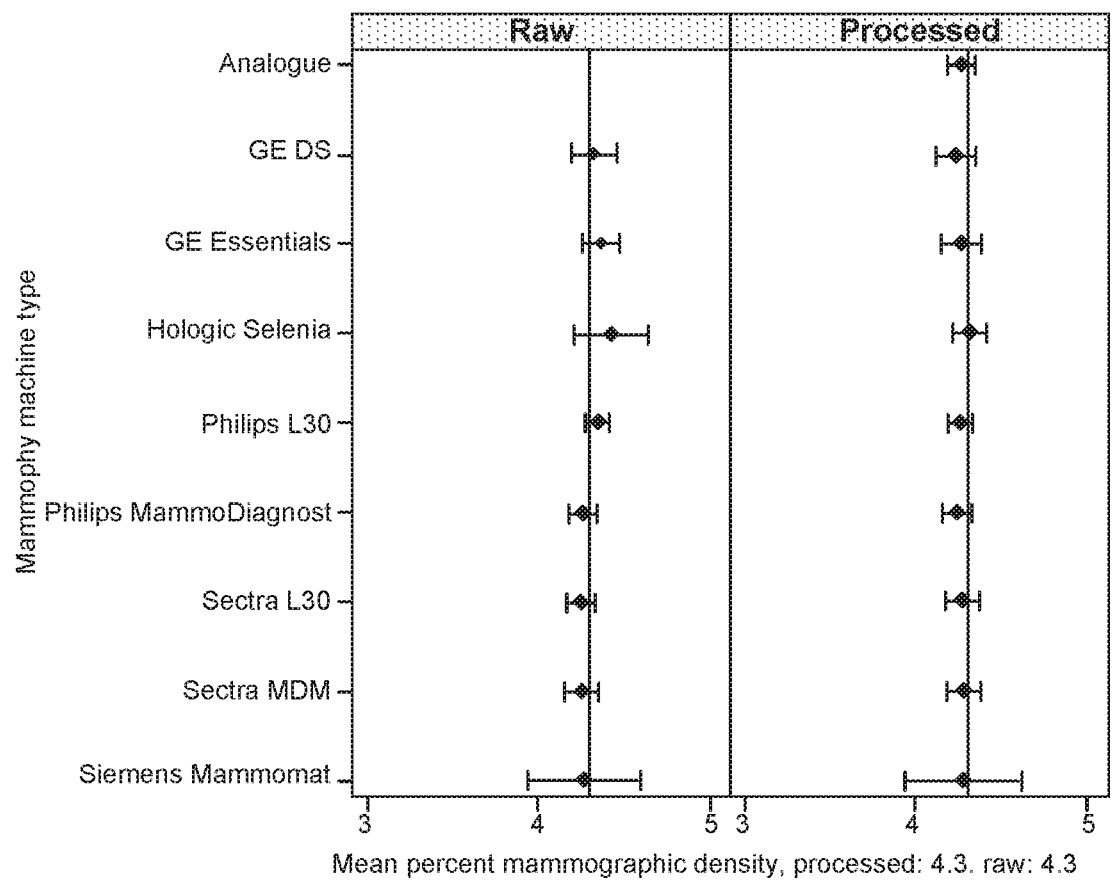
FIG. 7 shows comparison of STRATUS mean percent mammographic densities and 95% confidence intervals between eight types of mammography machines with raw and processed mammograms; and the analogue mammogram type. Percent mammographic density was square root transformed (to a 0-10 scale) and adjusted for age, BMI, and a breast compression score. The breast compression score was calculated using the x-ray tube voltage of the machine, the breast compression force, the breast compression thickness recorded during the compression, and mammography machine specific constants for calibrating machine specific reporting on breast thickness. 39,186 women with processed images (also counting analog images) were included as were 31,075 women with raw images. 28,908 women had both processed and raw mammograms. The number of mammograms was limited for the Siemens machine (N=136 processed and N=113 raw) and the Hologic machine (N=1,098 processed and N=214 raw) due to missing information on BMI for the women.

[1]Digital images
[2]Analogue images
Total women in the three study samples: 2,876 cases and 5,817 controls The correlations between the measures on the raw and processed mammogram were close to 0.9 on all mammography machines (FIG. 5). The correlations increased with increasing number of images used in the density training session and reached Spearman r=0.933 (min=0.923, max=0.936) when training was based on up to 4,000 images per machine. The Bland-Altman fit plot showed agreement between the raw and processed mammograms and the standardized mean difference was 0.01 with standard deviation 0.28 (FIG. 6). No significant differences were found in mean percent mammographic densities between the nine mammogram types after adjusting for age, BMI, x-ray tube voltage, and breast thickness, p>0.05, (FIG. 7). The same non-significant differences between mammography machines were seen when BMI was substituted with breast area as adjustment factor (data not shown).

The odds-ratios for percent density in the full model ranged between 1.5 (CI 1.3-1.7) and 1.7 (CI 1.6-1.8) per standard deviation in the three studies; and the combined odds-ratio was OR 1.6 (1.3-1.8) (Table 2).

TABLE 2

Odds-ratios and 95% confidence-intervals of breast cancer in three unique case-control study samples contrasting the performance of estimates per standard deviation from density measures in processed, raw, and analogue mammograms

| | Model 1[5] | Model 2[6] | Model 3[7] |
| --- | --- | --- | --- |
| 1a. KARMA (processed)[1] | 1.6 (1.5-1.7) | 1.7 (1.6-1.8) | 1.7 (1.6-1.8) |
| 1b. KARMA (raw)[2] | 1.6 (1.5-1.7) | 1.7 (1.6-1.8) | 1.7 (1.6-1.8) |
| 2. LIBRO1/KARMA (processed/analogue)[3] | 1.5 (1.4-1.6) | 1.6 (1.4-1.8) | 1.6 (1.4-1.8) |
| 3. LIBRO1/SASBAC (analogue)[4] | 1.5 (1.3-1.7) | 1.5 (1.3-1.8) | 1.5 (1.3-1.7) |
| Study samples combined | 1.5 (1.3-1.6) | 1.6 (1.3-1.8) | 1.6 (1.3-1.8) |

[1]433 cases and 1,732 controls with density measurements from processed mammograms
[2]433 cases and 1,732 controls with density measurements from raw mammograms
[3]2,443 cases with density measurement from processed mammograms and 2,999 controls with density measurements from analogue mammograms
[4]1,194 cases and 1,086 controls with density measurement from analogue mammograms
[5]Model 1 - percent density and age
[6]Model 2 - percent density, age, and BMI
[7]Model 3 - percent density, age, BMI, ever use of HRT, menopause status, and family history of breast cancer The discrimination performance of the full model ranged between AUC 0.60 (CI 0.57-0.63) and 0.63 (CI 0.60-0.65) in the three study samples; and the combined AUC for the three study samples was 0.62 (0.60-0.64) (Table 3).

TABLE 3

Discrimination performance (AUC) and 95% confidence intervals in three unique case - control study samples contrasting the performance of estimates from density measures in processed, raw, and analogue mammograms

| | Model 1[5] | Model 2[6] | Model 3[7] |
| --- | --- | --- | --- |
| 1a. KARMA (processed)[1] | 0.59 (0.55-0.63) | 0.62 (0.59-0.65) | 0.63 (0.60-0.65) |
| 1b. KARMA (raw)[2] | 0.59 (0.55-0.63) | 0.62 (0.59-0.65) | 0.63 (0.60-0.65) |
| 2. LIBRO1/ KARMA (processed/ analogue)[3] | 0.59 (0.55-0.62) | 0.60 (0.57-0.64) | 0.62 (0.59-0.64) |
| 3. LIBRO1/ SASBAC (analogue)[4] | 0.58 (0.55-0.62) | 0.59 (0.55-0.63) | 0.60 (0.57-0.63) |
| Study samples combined | 0.59 (0.55-0.62) | 0.60 (0.59-0.63) | 0.62 (0.60-0.64) |

TABLE 3-continued

Discrimination performance (AUC) and 95% confidence intervals in three unique case - control study samples contrasting the performance of estimates from density measures in processed, raw, and analogue mammograms

| | Model 1[5] | Model 2[6] | Model 3[7] |
|---|---|---|---|

[1]433 cases and 1,732 controls with density measurements from processed mammograms
[2]433 cases and 1,732 controls with density measurements from raw mammograms
[3]2,443 cases with density measurement from processed mammograms and 2,999 controls with density measurements from analogue mammograms
[4]1,194 cases and 1,086 controls with density measurement from analogue mammograms
[5]Model 1 - percent density and age
[6]Model 2 - percent density, age, and BMI
[7]Model 3 - percent density, age, BMI, ever use of HRT, menopause status, and family history of breast cancer The aligned percent density measures showed a significantly lower variability compared to measures of non-aligned dense area (SD 8.0 vs. 28.6, p<0.001) in the 11,409 women with two consecutive mammograms taken within minutes (Table 4).

TABLE 4

Comparison of variability in density measurements of non-aligned and aligned mammograms taken at two time-points

| Time series | Non-aligned | Aligned | p-value[3] |
|---|---|---|---|
| Mammograms within minutes apart (last minus first)[1] | | | |
| Difference in percent density, mean (SD) | 0.3 (20.6) | 0.1 (10.4) | <0.001 |
| Difference in dense area cm2, mean (SD) | 0.3 (28.6) | 0.0 (8.0) | <0.001 |
| Mammograms up to two years apart (last minus first)[2] | | | |
| Yearly change in percent density, mean (SD) | −1.5 (5.0) | −0.9 (4.3) | <0.001 |
| Yearly change in dense area cm2, mean (SD) | −1.8 (6.8) | −1.8 (6.8) | 0.99 |

[1]N = 11,409 women with digital images. Images taken on average 1 minute apart. Mean age 57 (SD 9,8), BMI26 (SD 4.7).
[2]N = 55,073 women with digital processed images. Images taken on average 2.0 years apart. Mean age 55 (SD 10.0), BMI 25 (SD 4.2).
[3]The Levene's test tested for equality of variances between the measures of aligned and non-aligned mammograms. All density measurement differences were normally distributed.

The Spearman rank coefficient r was used to calculate the correlation between the density measurements of aligned and non-aligned mammograms. The correlation between measures from aligned and non-aligned mammograms taken up to two years apart was r=0.64 for percent density and r=0.60 for dense area.

When comparing yearly change in percent density in 55,073 women that had two mammograms taken 1-2 years apart, percent density but not dense area showed significantly lower average yearly decrease in the aligned images, 0.9 vs. 1.5 (SD 4.3 vs. 5.0), p<0.001, Table 4. In FIGS. 8A and 8B, the yearly, aligned and non-aligned, percent mammographic density change is plotted for the 55,073 women. The black fitted line shows the yearly average percent density change with 95% CI and the circled dots the density averages by age at baseline. The grey curves show the density change stratified by BMI sub groups defined at baseline. It can be seen that the biggest difference between aligned and non-aligned measures is seen during women's fertile part of life and that the confidence intervals are smaller for the aligned measures.

Discussion

The present invention discloses a tool that enables comparison of mammographic density changes over time without being restricted by type of mammogram or technical differences between images. STRATUS performs high-throughput measurements of mammographic density on mammograms from different mammography machines and mammogram types. As a consequence, risk assessments were not influenced by type of image when density risk association was estimated in three independent study samples including a combination of different types of mammograms. Further, the alignment protocol reduced the non-biological variability between mammograms.

Mammographic density is a strong marker of breast cancer risk with a discrimination performance comparable to established risk models, which combine information on hormonal exposures and family history of breast cancer (Eriksson M et al.; A clinical model for identifying the short-term risk of breast cancer; Breast Cancer Res. 2017 Mar. 14; 19(1):29). Several commercial software measures mammographic density, but all need raw images. The present invention discloses that with STRATUS that image types does not influence risk estimates discriminatory performance (Tables 2 & 3).

There are several reasons for identifying the true density change over time. A longitudinal study showed that individual differences in mammographic density changes over time were not associated with breast cancer risk (Lokate M., Stellato R. K. et al.; Age-related Changes in Mammographic Density and Breast Cancer Risk; American Journal of Epidemiology Advance Access published May 22, 2013, DOI: 10.1093/aje/kws446). This result was however based on non-aligned images. As revealed in FIG. 3, technical differences between mammograms influence the comparison of density measurements over time. This is particularly true for premenopausal women which could be a reflection of the change in breast size (Hussain Z., Roberts N.; Estimation of breast volume and its variation during the menstrual cycle using MRI and stereology; Br. J. Radiol. 1999 March, 72(855), 236-45), percent density (Chan S, SU MY. et al.; Menstrual cycle-related fluctuations in breast density measured by using three-dimensional MR imaging; Radiology 2011 December, 261(3):744-51), and dense area (Iversen A., Frydenberg H. et al.; Cyclic endogenous estrogen and progesterone vary by mammographic density phenotypes in premenopausal women; Eur. J. Cancer Prev. 2016 January, 25(1):9-18) during the menstrual cycle (Hovhannisyan G, Chow L et al.; Differences in measured mammographic density in the menstrual cycle; Cancer Epidemiol Biomarkers Prev. 2009 July; 18(7):1993-9).

Breast size is also strongly influenced by BMI which in turn is strongly associated with estrogen levels in pre- and postmenopausal women (Gretchen L. Gierach et al.; Relationship of Serum Estrogens and Metabolites with Area and Volume Mammographic Densities; Horm Cancer. 2015 June; 6(0): 107-119). This means that aligned density measures are potentially influenced not only by technical imaging differences, but changing BMI over time.

Another reason to study density change over time is that several studies have shown that density change is a remarkably good proxy for treatment response in the adjuvant and preventive setting (Mallick S, Benson R, Julka P K; Breast cancer prevention with anti-estrogens: review of the current evidence and future directions; Breast Cancer. 2016 March; 23(2):170-7). A decrease in mammographic density by 20% during the first two years of adjuvant therapy reduced breast cancer mortality by nearly 50% over the subsequent 15 years (Li J, Humphreys K, Eriksson L, Edgren G, Czene K, Hall P.; Mammographic density reduction is a prognostic marker of response to adjuvant tamoxifen therapy in postmenopausal patients with breast cancer.; J Clin Oncol. 2013 Jun. 20; 31(18):2249-56). This result was confirmed in later studies (Nyante S J, Sherman M E, Pfeiffer R M, Berrington de Gonzalez A, Brinton L A, Aiello Bowles E J, Hoover R N, Glass A, Gierach G L; Prognostic significance of mammographic density change after initiation of tamoxifen for E R-positive breast cancer; J Natl Cancer Inst. 2015 Feb. 6; 107(3)). Patients that benefits from adjuvant anti-hormonal therapy may therefore be identified. In consequence, non-responders could also be identified and selected for alternative treatments. In the preventive setting density change has also been demonstrated to be a good marker of tamoxifen response (Boyd N F, Byng J W, Jong R A, Fishell E K, Little L E, Miller A B, Lockwood G A, Tritchler D L, Yaffe M J.; Quantitative classification of mammographic densities and breast cancer risk: results from the Canadian National Breast Screening Study.; J Natl Cancer Inst. 1995 May 3; 87(9): 670-5). However, tamoxifen treatment is associated with side-effects, which are similar to menopausal symptoms, and in rare cases endometrial cancer and thromboembolism (Mallick S, Benson R, Julka P K; Breast cancer prevention with anti-estrogens: review of the current evidence and future directions; Breast Cancer. 2016 March; 23(2):170-7). It is therefore crucial to treat only the group of healthy women that respond to therapy and are likely to benefit with a decrease in breast cancer incidence.

Several techniques are available for aligning images (P. Thévenaz, U. E. Ruttimann, M. Unser, A Pyramid Approach to Subpixel Registration Based on Intensity, IEEE Transactions on Image Processing, vol. 7, no. 1, pp. 27-41, January 1998). Translation, rigid body, scaled rotation, affine, and bilinear transformation were tested. FIGS. 8A and 8B show that aligned density measurements capture the level and rate of density change is different compared to non-aligned density measures. The alignment protocol was developed to analyze several mammograms in a time series and do not be rely on the differences in pixel intensities, which can be seen between processed and raw or analogue images. FIG. 8A shows the mean mammographic density change (%) as a function of age and BMI for non-aligned images, and FIG. 8B shows the results for aligned images.

The strength of this study is that a large population based cohort with access to both raw and processed images form the same examinations and with to repeated and longitudinal measurements from the same women was studied. In addition, case—control study samples to combine cases and controls with different type of images from three unique Swedish studies were constructed.

Conclusion

STRATUS is a fully-automated tool that measures mammographic density from mammograms obtained from a variety of sources (raw and processed digital images, analog films). The added alignment feature provided by STRATUS improves longitudinal measurements of mammographic density. Given that an increasing number of mammograms are stored in the screening and clinical setting, STRATUS-derived mammographic density is a useful tool for risk prediction and treatment response in research and clinical praxis.

Example 5

Randomized, Double Blinded, Six Armed Placebo Controlled Study of Low Dose Tamoxifen Primary objective of the study is to identify the minimal dose of tamoxifen that is non-inferior in its ability to reduce mammographic density compared to 20 mg tamoxifen. Secondary objectives will be to assess the drop-out level and the level of side effects in the intervention arms compared to the 20 mg arm. Tertiary objectives will be to relate levels of tamoxifen metabolites, proteins, lipids and hormones in blood and changes in breast tissue to tamoxifen doses, genetic polymorphism in germline DNA and relate it to the other tertiary objectives such as mammographic density and levels of side effects in relation to tamoxifen dose.

1440 healthy female subjects, ages 40 to 74, all attending the Swedish national mammography screening program, will also be invited to participate in the study. To be included in the study, the subjects have to have a negative mammogram within 3 months from inclusion. To be eligible for the study, the subjects must have a measurable mammographic density, i.e. ≥4.5% density (volumetric) measured by Volpara. This level is equivalent to mammographic density The Breast Imaging Reporting and Data System (BI-RADS) A. Women recalled after a mammography screen will not be included in this study. FIG. 9 provides the study design.

Briefly, subjects will be engaged in the study for a period of 6 months. Some participants will be engaged in the study for additional 6 months or follow study. However, all subjects will be on tamoxifen medication for 6 months.

On day 0 (baseline) of the study, women fulfilling the inclusion and exclusion criteria will be randomized to one of the six treatment arms (6 cohorts): tamoxifen 20 mg, 10 mg, 5 mg, 2.5 mg, 1 mg or placebo. All investigational product (tamoxifen and placebo) will be provided as a tablet for oral administration and provided in blisters. All treatments will be on a daily basis for 6 months. The women will receive a sufficient amount of tamoxifen in order to take one tablet daily during 6 months. Compliance will be assessed throughout the study by i) calculating the number of tablets remaining at the final visit at the Karma Study Centre and comparing with the expected usage, ii) by web-questionnaires targeting adherence to therapy. The participant is defined as a complier if more than 80% of the tablets are taken.

On day zero of the study (baseline), 24 ml blood will be collected from each subject. The blood will be analyzed for plasma hormones, plasma proteins, metabolic markers. In addition, DNA will be extracted and plasma aliquots will be biobanked for later analyses. The subjects will be asked if they allow to have two biopsies of the normal breast tissue taken at month 0 and 6 Subjects willing to have two biopsies will be have a biopsy performed at baseline. Participation in the biopsy part of the study is not mandatory.

The participants will fill out three web-based questionnaires One questionnaire will be regarding several lifestyle factors that influence risk of breast cancer such as age at first birth, breast-feeding, etc., demographic, medical history, quality-of-life, and concomitant medication will be provided to the participants. Second baseline questionnaire will be regarding general symptoms and tamoxifen related symptoms. The third questionnaire deals with adherence to therapy. Measurement of weight, length and waist will be taken to establish the body mass index (BMI) of the subject. The web based questionnaires could be answered using a computer or a specially developed app, Karm-app. Instructions will be given on how to use and report events by the Kann-app. Reminders will be sent out at months 1, 3 and 6 (end of study) to answer questions regarding general symptoms, tamoxifen related symptoms, compliance and health care contact connected to possible side effects.

At the end of 6 months, 24 ml blood will be collected from each subject. Tamoxifen metabolites, plasma hormones, plasma proteins, metabolic markers will be measured. Mammograms (one image per breast only for density measurement purposes) of each subject will be taken. Measurement of weight, length and waist for determining BMI at the end of 6 months period will be performed. A second biopsy will be performed for the subjects who had a first biopsy taken at baseline.

Primary endpoint will to measure change in mammographic density and levels of side effects after 6 months. In particular, non-inferiority in the proportion of women in the intervention arms (placebo, 1 mg, 2.5 mg, 5 mg, 10 mg) who have a density reduction as great as or greater (after 6 months) than the median density reduction in the 20 mg arm will be tested. The primary analysis will be performed on an intention to treat (ITT) basis. Changes in area based mammographic density will be determined. A "responder" is defined as a woman whose mammographic density decreases between baseline and 6 months exceeds the response threshold. Response threshold is defined as the median decrease in mammographic density of women in the 20 mg tamoxifen arm.

Differences in the proportion of drop-outs after 6 months in the intervention arms compared to the 20 mg arm will be measured as a secondary endpoint. Levels of tamoxifen metabolites, proteins, lipids and hormones in blood, breast tissue changes, genetic polymorphism in germline DNA and mammographic density and levels of side effects 6 months after tamoxifen cessation will be measured as tertiary endpoint.

Safety endpoints will be summarized by dose cohorts, with placebos pooled across cohorts. Treatment-Emergent Adverse Events (TEAEs) will be coded using the latest version of MedDRA by System Organ Class (SOC) and Preferred Term, classified from verbatim terms. The incidence and frequency of TEAEs, and Serious Adverse Effects (SAEs), will be summarized by cohort according to SOC and Preferred Terms, and by severity and relationship. The duration of AEs was determined and included in listings, along with the action taken and outcome. Vital signs, ECG and safety laboratory parameters will be summarized at each scheduled time point using descriptive statistics. Post-dose assessments will be compared with baseline measurements. The incidence of laboratory abnormalities will be summarized. Physical examination findings will be presented in listings.

Mean and individual tamoxifen serum concentration-time curves will be tabulated for each dose cohort. Pharmacokinetic parameters will be determined for each participant and summarized by cohort using descriptive statistics (arithmetic means, standard deviations, coefficients of variation, sample size, minimum, maximum and median). In addition, geometric means will be calculated for AUC and Cmax. Analyses using linear models will be performed to assess dose proportionality, time dependence and accumulation, and attainment of steady state (multiple dose).

Example 6

Clinical Presentation of Mammographic Density Change in Response to Tamoxifen Treatment Mammographic density was measured for left and right breasts for all mammograms at baseline and over the follow-up monitoring time. Relative density change was calculated for each follow-up mammogram as the follow-up density measurement minus the baseline density measurement, in turn divided by the baseline density measurement.

Figure 4A:
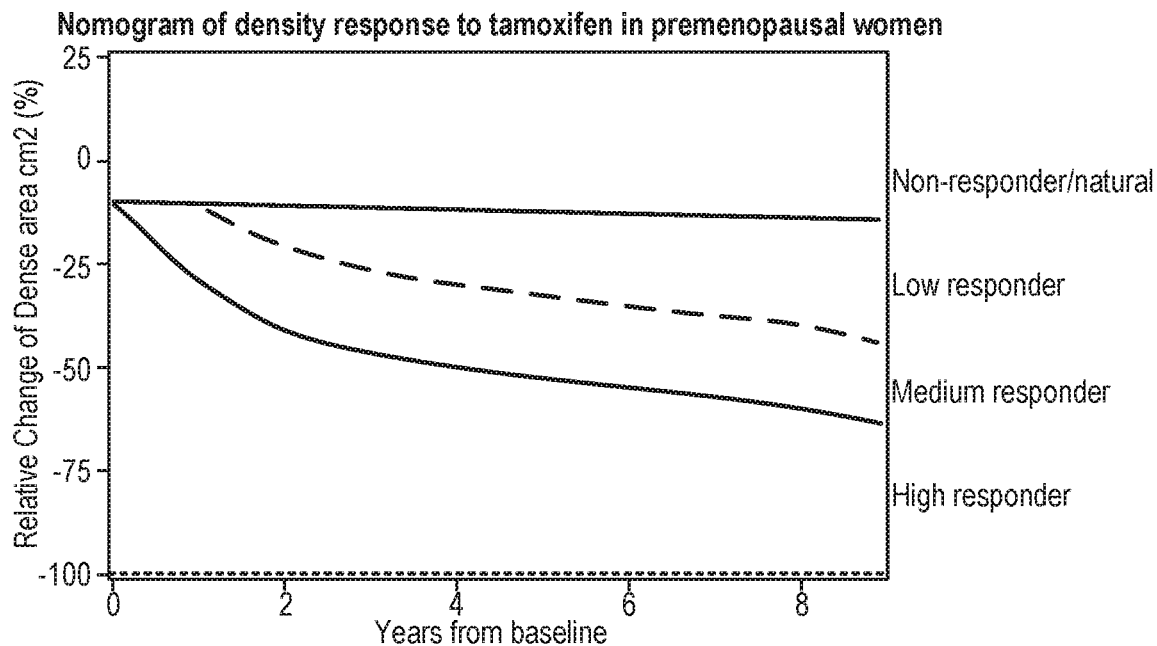
FIGS. 4A and 4B show nomograms of density change in response to treatment in pre- and postmenopausal women.
Figure 4B:
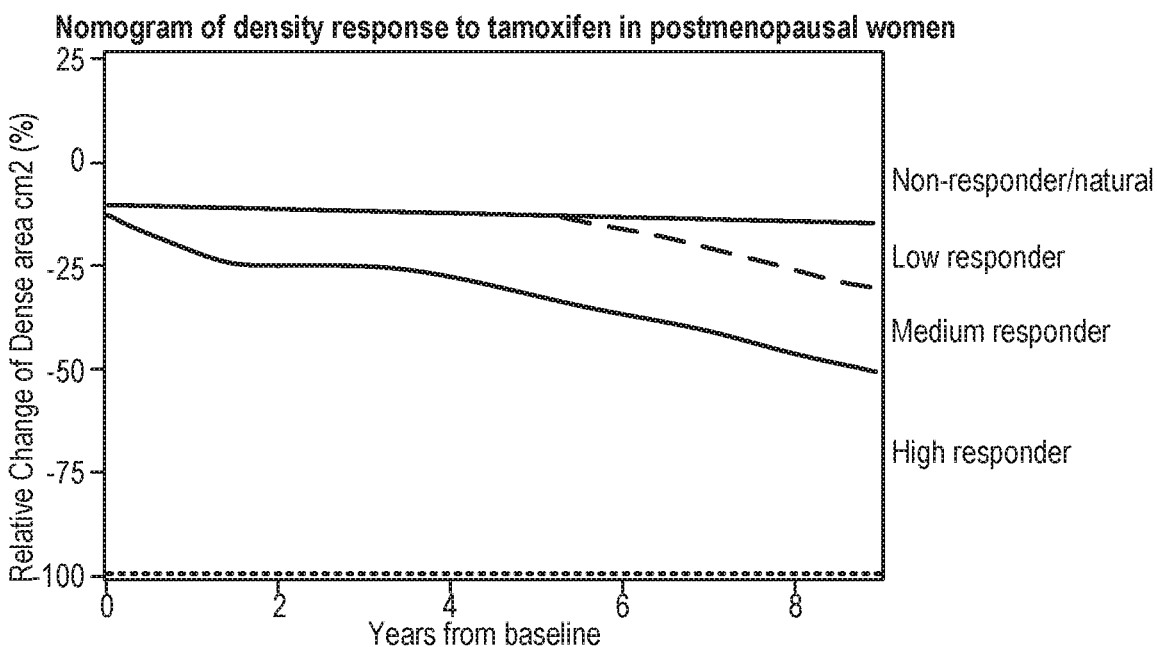

The relative density change was categorized into four categories in the tamoxifen treatment cohort and is visualized as a nomogram for pre- and postmenopausal women (FIGS. 4A and 4B). The non-responding density category was defined as densities from mammograms that did not decrease more than 10% relative to baseline. The density change that naturally occurs in the breast due to involution was added to this number by adding 0.52% (2/38) decrease per year for premenopausal women and 0.45% (1/21) decrease per year for postmenopausal women. This was calculated as 2 cm2 dense area, and 1 cm2 dense area, yearly decrease in pre- and postmenopausal respectively (Eriksson 2018). This was divided by the average dense area among pre- and postmenopausal women respectively, i.e. 38 cm2 and 21 cm2.

The medium density decrease category was defined as the average decrease observed in the tamoxifen treatment cohort. A margin of 10% is used around the average over time (FIGS. 4A and 4B). The low responding density category was defined as the densities between the non-responders and the average responders. The high density decrease category was defined as the densities that decreased more than the average category.

Based on the above, each woman can be categorized into one of the four categories as the average of the woman's time series response categories from baseline to the end of follow-up.

A clinician can monitor each woman on the nomogram through markings of the density change over time. The monitoring can be included in evaluating a treatment regimen or designating a new treatment regimen.

The foregoing discussion has been presented for purposes of illustration and description. The foregoing is not intended to limit the disclosure to the form or forms disclosed herein. Although the disclosure includes the description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

It is to be understood that compositions comprising tamoxifen free base and salts thereof disclosed herein may be prepared with synthetically prepared tamoxifen as well as isolated tamoxifen. It is to be further understood that dosing of the subjects is based on amount tamoxifen present in the composition.

All publications, patents and patent applications referred to herein are incorporated by reference in their entirety to the same extent as if each individual publication, patent or patent application was specifically and individually indicated to be incorporated by reference in its entirety.

What is claimed is:

1. A method of treatment of a subject having or is at risk of having breast disorder, comprising:
   (a) receiving, in a computer processing system, data input comprising a plurality of breast images of a subject and image metadata;
   (b) applying an alignment algorithm to the plurality of breast images, the alignment algorithm comprising:

(i) labeling pixels in the plurality of breast images as breast area based on a polynomial fit to a corresponding region of one or more kernel images to generate a plurality of binary masks, thereby performing a thresholding method on the plurality of breast images marking the breast area in the plurality of breast images;
(ii) superimposing the breast area in each of the plurality of breast images in layers;
(iii) moving binary masks in breast area markings towards each other to an optimal position for alignment of the breast areas where pixel intensities of the binary masks show minimal difference relative to one another using least square means; and
(iv) generating by computer an aligned image from the optimal position comprising an area of mutual image information that is the resulting breast area of the aligned image; and
(c) administering a treatment regimen to the subject based on the aligned image.

2. The method of claim 1, further comprising extracting texture features from mutual image information of the breast area in an aligned image or each of the plurality of breast images.

3. The method of claim 2, wherein the texture features are further stratified and compiled to generate feature variables.

4. The method of claim 1 wherein the image metadata comprises reported thickness of a compressed breast, reported x-ray tube voltage of a machine, mammography machine type, and machine specific breast thickness compression constants, or a combination thereof.

5. The method of claim 1 further comprising applying a breast compression score algorithm to the plurality of breast images based on image metadata to generate a breast compression score.

6. The method of claim 1, further comprising generating a biomedical output comprising density measures from the area of mutual image information in the aligned image, determined based on a statistical machine learning model.

7. The method of claim 1, wherein the breast image is a 2D image, a 3D image, an MRI image, a CT-Scan image, or a mammographic image.

8. The method of claim 7, wherein the mammographic image is a digital image, an analog image, a raw image, a processed image, a normalized image, or a digitally scaled image.

9. The method of claim 1, further comprising:
generating a first aligned image and a second aligned image of the subject's breast; and
comparing average density measures from the area of mutual image information of the second aligned image relative to average density measures from the area of mutual image information of the first aligned image.

10. The method of claim 1, further comprising:
wherein the first aligned image is of the subject's right breast and the second aligned image of the subject's left breast; or
wherein the first aligned image of the subject's breast is from a reference time and the second aligned image is from the target time.

11. The method of claim 1, further comprising providing for presentation information to facilitate treatment of the subject based at least in part on the aligned image.

12. The method of claim 1, further comprising providing for graphical presentation of diagnostic information to facilitate treatment of the subject based at least in part on the aligned image such that the information improves detection of changes over time relative to comparable information based on non-aligned images.

13. A non-transitory computer-readable medium storing thereon executable instructions, that when executed by a computer, causes the computer to execute a method of designating a treatment regimen for a subject having or is at risk of having breast, disorder, the method comprising:
(a) obtaining a data input comprising a plurality of breast images and image metadata;
(b) applying an alignment algorithm to the plurality of breast images, the alignment algorithm comprising:
(i) labeling pixels in the plurality of breast images as breast area based on a polynomial fit to a corresponding region of one or more kernel images to generate a plurality of binary masks, thereby performing a thresholding method on the plurality of breast images marking breast area in the plurality of breast images;
(ii) superimposing the breast area in each of the plurality of breast images in layers;
(iii) moving binary masks in breast area markings towards each other to an optimal position of alignment where pixel intensities of the binary masks show minimal difference relative to one another using least square means; and
(iv) generating an aligned image from the optimal position comprising an area of mutual image information that is the resulting breast area of the aligned image; and
(c) designating, by a software module, a treatment regimen for the subject based on the aligned image.

14. The non-transitory computer-readable medium of claim 13, further comprising (d) presenting the density measures over a time period.

15. A non-transitory computer-readable storage medium encoded with a computer program including instructions executable by a digital processing device comprising:
(a) a software module configured to obtain input data comprising a plurality of breast images and image metadata of a subject;
(b) a software module configured to apply an alignment algorithm comprising
(i) labeling pixels in the plurality of breast images as breast area based on a polynomial fit to a corresponding region of one or more kernel images to generate a plurality of binary masks, thereby performing a thresholding method on the plurality of breast images to mark breast area in the breast images;
(ii) superimposing the breast area in each of the plurality of breast images in layers;
(iii) moving binary masks towards each other to an optimal position where pixel intensities of the binary masks show minimal difference relative to one another using least square means;
(iv) generating an aligned image from the optimal position comprising an area of mutual image information that is the resulting breast area of the aligned image; and
(c) a software module configured to designate a treatment regimen for a subject diagnosed with a breast disorder or at risk of having a breast disorder based on the aligned image.

16. The storage medium of claim 15, further comprising (d) presenting the density measures over a time period.

17. The storage medium of claim 15, further comprising one or more software modules configured to generate a breast compression score by applying a breast compression score algorithm to the mutual image information.

18. A computer-implemented system, comprising:
(a) a digital processing device comprising an operating system configured to perform executable instructions, and a memory device;
(b) a computer program including instructions executable by a digital processing device comprising;
(i) a software module configured to receive a plurality of mammographic images of a subject;
(ii) a software module configured to apply alignment algorithm to the plurality of images, the alignment algorithm comprising:
(A) labeling pixels in the plurality of breast images as breast area based on a polynomial fit to a corresponding region of one or more kernel images to generate a plurality of binary masks, thereby performing a thresholding method on the plurality of breast images to mark breast area in the breast images;
(B) superimposing the breast area in each of the plurality of breast images in layers;
(C) moving binary masks towards each other to an optimal position where pixel intensities of the binary masks show minimal difference relative to one another; and
(D) generating an aligned image from the optimal position comprising an area of mutual image information that is the resulting breast area of the aligned image; and
(iii) a software module configured to designate a treatment regimen for a subject diagnosed with a breast disorder or at risk of having a breast disorder based on the aligned image.

19. The system of claim 18, further comprising one or more software modules configured to generate a breast compression score.

20. The system of claim 18, further comprising one or more software modules configured to generate a biomedical output comparing the breast density measures of the area of mutual image information of aligned images over time.

21. The system of claim 18, further comprising one or more software modules configured to diagnose, predict, or monitor the status or outcome of breast density masking or breast cancer or both in a subject and designate a subject as a tamoxifen-responder or a tamoxifen-non-responder.

22. The method of claim 1, wherein the treatment regimen comprises delivering to the subject an effective amount of low-dose tamoxifen.

23. The method of claim 22, wherein the low-dose tamoxifen is 0.5 mg. 1 mg, 1.5 mg, 2 mg, 2.5 mg. 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg of tamoxifen per unit dose.

24. The method of claim 22, wherein the low-dose tamoxifen is administered orally, topically, intraductally, or parenterally.

25. The method of claim 24, wherein the low-dose tamoxifen reduces the breast disorder.

26. A computer-implemented method, comprising:
(a) receiving, in a computer processing system, data input comprising a plurality of breast images of a subject and image metadata; and
(b) applying an alignment algorithm to the plurality of breast images, the alignment algorithm comprising:
(i) labeling pixels in the plurality of breast images as breast area based on a polynomial fit to a corresponding region of one or more kernel images to generate a plurality of binary masks, thereby performing a thresholding method on the plurality of breast images marking breast area in the plurality of breast images;
(ii) superimposing the breast area in each of the plurality of breast images in layers;
(iii) moving binary masks in breast area markings towards each other to an optimal position for alignment of the breast areas where pixel intensities of the binary masks show minimal difference relative to one another using least square means; and
(iv) generating by computer an aligned image from the optimal position comprising an area of mutual image information that is the resulting breast area of the aligned image.

* * * * *